(12) United States Patent
Shusta et al.

(10) Patent No.: US 9,629,801 B2
(45) Date of Patent: Apr. 25, 2017

(54) BLOOD-BRAIN BARRIER TARGETING ANTIBODIES

(71) Applicant: Wisconsin Alumni Research Foundation, Madison, WI (US)

(72) Inventors: Eric V. Shusta, Madison, WI (US); Angela R Jones, College Park, MD (US); Charles C. Stutz, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/593,102

(22) Filed: Jan. 9, 2015

(65) Prior Publication Data
US 2015/0196663 A1  Jul. 16, 2015

Related U.S. Application Data

(60) Provisional application No. 61/925,809, filed on Jan. 10, 2014.

(51) Int. Cl.
*A61K 9/00* (2006.01)
*A61K 39/00* (2006.01)
*C07K 16/28* (2006.01)

(52) U.S. Cl.
CPC ............ *A61K 9/0085* (2013.01); *C07K 16/28* (2013.01); *A61K 2039/505* (2013.01); *C07K 2317/21* (2013.01); *C07K 2317/622* (2013.01); *C07K 2317/77* (2013.01)

(58) Field of Classification Search
None
See application file for complete search history.

(56) References Cited

U.S. PATENT DOCUMENTS

| | | | |
|---|---|---|---|
| 7,744,879 B2 | 6/2010 | Shusta et al. | |
| 7,981,417 B2 | 7/2011 | Shusta et al. | |
| 2005/0142141 A1* | 6/2005 | Pardridge | A61K 47/48561 424/178.1 |
| 2010/0158920 A1* | 6/2010 | Ludwig | A61K 39/39541 424/142.1 |
| 2012/0308573 A1* | 12/2012 | Benson | C07K 16/244 424/139.1 |

OTHER PUBLICATIONS

PNAS 2016 "Author submission guidelines" excerpt. Accessed from pnas.org on Apr. 29, 2016.*
Pubmed 2016 "list of references citing Sheets" accessed from ncbi.nlm.nih.gov on Apr. 29, 2016.*
Sheets 1998 "Efficient construction of a large nonimmune phage antibody library: the production of high-affinity human single chain antibodies to protein antigens" PNAS 95:6157-6162.*
Abbott, et al., Overview and Introduction: The Blood-Brain Barrier in Health and Disease, Epilepsia, 2012, 53(Suppl. 6):1-6.
Adams, et al., Avidity-Mediated Enhancement of In Vivo Tumor Targeting by Single-Chain Fv Dimers, Clin. Cancer Res., 2006, 12(5)1599-1605.
Bickel, et al., Delivery of Peptides and Proteins Through the Blood-Brain Barrier, Adv. Drug Deliv. Rev., 2001, 46 (1-3):247-279.
Calabria, et al., Blood-Brain Barrier Genomics and Proteomics: Elucidating Phenotype, Identifying Disease Targets and Enabling Brain Drug Delivery, Drug Discovery Today, 2006, 11(17-18):792-799.
Calabria, et al., Puromycin-Purified Rat Brain Microvascular Endothelial Cell Cultures Exhibit Improved Barrier Properties in Response to Glucocorticoid Induction, J. Neurochem., 2006, 97(4):922-933.
Calabria, et al., A Genomic Comparison of In Vivo and In Vitro Brain Microvascular Endothelial Cells, J. Cereb. Blood Flow Metab., 2008, 28(1):135-148.
Chen, et al., Molecular Signatures of Disease Brain Endothelia Provide New Sites for CNS-Directed Enzyme Therapy, Nat. Med., 2009, 15(10):1215-1218.
Daneman, et al., The Mouse Blood-Brain Barrier Transcriptome: A New Resource for Understanding the Development and Function of Brain Endothelial Cells, PLoS One, 2010, 5(10):e13741, 16 pp.
Florea, et al., Identification of an Internalising Peptide in Differentiated Calu-3 Cells by Phage Display Technology; Application to Gene Delivery to the Airways, J. Drug Targeting, 2003, 11(7):383-390.
Heitner, et al., Selection of Cell Binding and Internalizing Epidermal Growth Factor Receptor Antibodies from a Phage Display Library, J. Immunol. Methods, 2001, 248(1-2):17-30.
Huie, et al., Antibodies to Human Fetal Erythroid Cells from a Nonimmune Phage Antibody Library, Proc. Natl. Acad. Sci. USA, 2001, 98(5):2682-2687.
Jones, et al., Blood-Brain Barrier Transport of Therapeutics Via Receptor-Mediation, Pharmaceutical Research, 2007, 24(9):1759-1771.
Lajoie et al., Targeting Receptor-Mediated Transport for Delivery of Biologics Across the Blood-Brain Barrier, Review in Advance first posted online on Oct. 8, 2014, pp. 31.1-31.19.
Li, J., et al., Targeting the Brain with PEG-PLGA Nanoparticles Modified with Phage-Displayed Peptides, Biomaterials, 2011, 32(21):4943-4950.

(Continued)

*Primary Examiner* — Adam M Weidner
(74) *Attorney, Agent, or Firm* — Quarles & Brady, LLP

(57) ABSTRACT

This application discloses a BBB-selective antibody. The BBB-selective antibody comprises a protein encoded by a DNA sequence comprising SEQ ID NO:7 (CDRH1 of scFv 15), SEQ ID NO:8 (CDRH2 of scFv 15), SEQ ID NO:9 (CDRH3 of scFv 15), SEQ ID NO:10 (CDRL1 of scFv 15), SEQ ID NO:11 (CDRL2 of scFv 15) and SEQ ID NO:12 (CDRL3 of scFv 15) or a DNA sequence comprising SEQ ID NO:19 (CDRH1 of scFv 38), SEQ ID NO:20 (CDRH2 of scFv 38), SEQ ID NO:21 (CDRH3 of scFv 38), SEQ ID NO:22 (CDRL1 of scFv 38), SEQ ID NO:23 (CDRL2 of scFv 38) and SEQ ID NO:24 (CDRL3 of scFv 38). Preferably, the BBB-selective antibody comprises a protein encoded by SEQ ID NO:1 or 3.

12 Claims, 7 Drawing Sheets
(5 of 7 Drawing Sheet(s) Filed in Color)

(56) References Cited

OTHER PUBLICATIONS

Li, J.Y., et al., Blood-Brain Barrier Genomics, J. Cereb. Blood Flow Metab., 2001, 21(1):61-68.
Li, J.Y., et al., Rat Blood-Brain Barrier Genomics. II, J. Cereb. Blood Flow Metab., 2002, 22(11):1319-1326.
Lyck, et al, Culture-Induced Changes in Blood-Brain Barrier Transcriptome: Implications for Amino-Acid Transporters In Vivo, J. Cereb. Blood Flow Metab., 2009, 29(9):1491-1502.
Martin, et al., Nanomaterials in Analytical Chemistry, Analytical Chemistry, 1998, 70(9):322A-327A.
Muruganandam, et al., Selection of Phage-Displayed Llama Single-Domain Antibodies That Transmigrate Across Human Blood-Brain Barrier Endothelium, FASEB J., 2001, 16(2):240-242.
O'Connell, et al., Phage Versus Phagemid Libraries for Generation of Human Monoclonal Antibodies, J. Mol. Biology, 2002, 321(1):49-56.
Pardridge, et al., Transport of Human Recombinant Brain-Derived Neurotrophic Factor (BDNF) Through the Rat Blood-Brain Barrier In Vivo Using Vector Mediated Peptide Drug Delivery, Pharm. Res., 1994, 11(5):738-746.
Pardridge, et al., Human Insulin Receptor Monoclonal Antibody Undergoes High Affinity Binding to Human Brain capillaries In Vitro and Rapid Transcytosis Through the Blood-Brain Barrier In Vivo in the Primate, Pharm. Res., 1995, 12(6):807-816.
Perriere, et al., Puromycin-Based Purification of Rat Brain Capillary Endothelial Cell Cultures. Effect on the Expression of Blood-Brain Barrier-Specific Properties, J. Neurochem., 2005, 93(2):279-289.
Perriere, et al., A Functional In Vitro Model of Rat Blood-Brain Barrier for Molecular Analysis of Efflux Transporters, Brain Research, 2007, 1150:1-13.
Poul, et al., Selection of Tumor-Specific Internalizing Human Antibodies from Phage Libraries, J. Mol. Biology, 2000, 301(5)1149-1161.
Safdari, et al., Antibody Humanization Methods—A Review and Update, Biotechnology and Genetic Engineering Reviews, 2013, 29(2):175-186.
Saito, et al., Drug Delivery Strategy Utilizing Conjugation Via Reversible Disulfide Linkages: Role and Site of Cellular Reducing Activities, Adv Drug Deliv Rev., 2003, 55(2):199-215.
Sheets, et al., Efficient Construction of a Large Nonimmune Phage Antibody Library: The Production of High-Affinity Human Single-Chain Antibodies to Protein Antigens, Proc. Natl. Acad. Sci. USA, 1998, 95(11):6157-6162.
Shusta, et al., Vascular Genomics of the Human Brain, J. Cereb. Blood Flow Metab., 2002, 22(3):245-252.
Stewart, et al., Endothelial Vesicles in the Blood-Brain Barrier: Are They Related to Permeability?, Cell. Mol. Neurobiol., 2000, 20(2):149-163.
Stutz, et al., Combinatorial Approaches for the Identification of Brain Drug Delivery Targets, Current Pharmaceutical Design, 2014, 20(10):1564-1576.
Sugano, et al., Antibody Targeting of Doxorubicin-loaded Liposomes Suppresses the Growth and Metastatic Spread of Established Human Lung Tumor Xenografts in Severe Combined Immunodeficient Mice, Cancer Research, 2000, 50:6942-6949.
Trail, et al., Monoclonal Antibody Drug Immunoconjugates for Targeted Treatment of Cancer, Cancer Immunol Immunother, 2003, 52(5)328-337.
Verma, et al., Antibody Engineering: Comparison of Bacterial, Yeast, Insect and Mammalian Expression Systems, J Immunol Methods, 1998, 216(1-2):165-181.
Wang, et al., Mining a Yeast Library for Brain Endothelial Cell-Binding Antibodies, Nat. Methods, 2007, 4(2):143-145.
Wu, et al., Arming Antibodies: Prospects and Challenges for Immunoconjugates, Nature Biotechnology, 2005, 23 (9)1137-1146.
Zhou, et al., Identification of Target and Function Specific Antibodies for Effective Drug Delivery, Therapeutic Antibodies, vol. 525 of the series Methods in Molecular Biology, 2008, pp. 145-160 [Abstract Only].

\* cited by examiner

FIGURE 1 A-C

FIGURE 2 A-C scFv 15

Germline Heavy Chain: Human immunoglobulin heavy variable 3-7

Germline Light Chain: Human immunoglobulin lambda variable 3-19

DNA Sequence: 708 base pairs

CAGGTGCAGCTGGTGGAGTCTGGGGGAGGCTTGGTCCAGCCTGGGGGGTCCCTGAGACTCTCCTGTGCAG
CCTCTGGATTCACCTTTAGTAACTATTGGATGACCTGGGGCCGCCAGGCTCCAGGGAAGGGGCTGGAGTG
GGTGGCCATCATAAGCCAAGATGGAAGTGAGAAATACTATGTGGACTCTGTGCAGGGCCGATTCACCATC
TCCAGAGACAACGCGAAGAACTCACTGTATCTGCAAATGAACAGCCTGACAGCCGAAGACACGGCTGTGT
ATTACTGTGCGAGAGATCGATATGATTACTGGGGCCAGGGCACCCTGGTCACCGTCTCCTCAGGTGGAGG
CGGTTCAGGCGGAGGTGGCTCTGGCGGTGGCGGATCGAATTTTATGCTGACTCAGGACCCTGCTGTGTCT
GTGGCCTTGGGACAGACAGTCAGGATCACATGCCAAGGAGACAGCCTCAGAAGCTATTATGCAAGCTGGT
ACCAGCAGAAGCCAGGCCAGTCCCCTGTGCTGGTCATCTATCAAGATAACAAGCGGCCCTCAGGGATCCC
TGAGCGATTCTCTGGCTCCAAGTCTGGGAATACAGCCACTCTGACCATCAGCGGGACCCAGGCTATGGAT
GAGGCTGAGTATTTCTGTCAGGCGTGGGACAGCAGCGCTGTCGCGTTCGGCGGAGGGACCAAGGTCACCG
TCCTAGGT (SEQ ID NO:1)

DNA Sequence with CDR Labels

CAGGTGCAGCTGGTGGAGTCTGGGGGAGGCTTGGTCCAGCCTGGGGGGTCCCTGAGACTCTCCTGTGCAG
           |----------CDR H1 (SEQ ID NO:7)---|
CCTCTGGATTCACCTTTAGTAACTATTGGATGACCTGGGGCCGCCAGGCTCCAGGGAAGGGGCTGGAGTG
         |---------------------CDR H2 (SEQ ID NO:8)---------------|
GGTGGCCATCATAAGCCAAGATGGAAGTGAGAAATACTATGTGGACTCTGTGCAGGGCCGATTCACCATC

TCCAGAGACAACGCGAAGAACTCACTGTATCTGCAAATGAACAGCCTGACAGCCGAAGACACGGCTGTGT
          |----CDR H3---| (SEQ ID NO:9)
ATTACTGTGCGAGAGATCGATATGATTACTGGGGCCAGGGCACCCTGGTCACCGTCTCCTCAGGTGGAGG

CGGTTCAGGCGGAGGTGGCTCTGGCGGTGGCGGATCGAATTTTATGCTGACTCAGGACCCTGCTGTGTCT
                           |----------CDR L1 (SEQ ID NO:10)---|
GTGGCCTTGGGACAGACAGTCAGGATCACATGCCAAGGAGACAGCCTCAGAAGCTATTATGCAAGCTGGT
                                 |-------CDR L2------|(SEQ ID NO:11)
ACCAGCAGAAGCCAGGCCAGTCCCCTGTGCTGGTCATCTATCAAGATAACAAGCGGCCCTCAGGGATCCC

TGAGCGATTCTCTGGCTCCAAGTCTGGGAATACAGCCACTCTGACCATCAGCGGGACCCAGGCTATGGAT
          |----------CDR L3 (SEQ ID NO:12)|
GAGGCTGAGTATTTCTGTCAGGCGTGGGACAGCAGCGCTGTCGCGTTCGGCGGAGGGACCAAGGTCACCG

TCCTAGGT(SEQ ID NO:1)

Amino Acid Sequence: 236 residues

FIGURE 5

QVQLVESGGGLVQPGGSLRLSCAASGFTFSNYWMTWGRQAPGKGLEWVAIISQDGSEKYYVDSVQGRFTI
SRDNAKNSLYLQMNSLTAEDTAVYYCARDRYDYWGQGTLVTVSSGGGGSGGGGSGGGGSNFMLTQDPAVS
VALGQTVRITCQGDSLRSYYASWYQQKPGQSPVLVIYQDNKRPSGIPERFSGSKSGNTATLTISGTQAMD
EAEYFCQAWDSSAVAFGGGTKVTVLG

Amino Acid Sequence with CDR Labels

CDR H1 (SEQ ID NO:13)                   CDR H2 (SEQ ID NO:14)
QVQLVESGGGLVQPGGSLRLSCAASGFTFSNYWMTWGRQAPGKGLEWVAIISQDGSEKYYVDSVQGRFTI
                                CDR H3 (SEQ ID NO:15)
SRDNAKNSLYLQMNSLTAEDTAVYYCARDRYDYWGQGTLVTVSSGGGGSGGGGSGGGGSNFMLTQDPAVS
           CDR L1 (SEQ ID NO:16)       CDR L2 (SEQ ID NO:17)
VALGQTVRITCQGDSLRSYYASWYQQKPGQSPVLVIYQDNKRPSGIPERFSGSKSGNTATLTISGTQAMD
        CDR L3 (SEQ ID NO:18)
EAEYFCQAWDSSAVAFGGGTKVTVLG   (SEQ ID NO:2)

scFv 38

Germline Heavy Chain: Human immunoglobulin heavy variable 3-30

Germline Light Chain: Human immunoglobulin kappa variable 1-12

DNA Sequence: 729 base pairs

CAGGTGCAGCTGGTGGAGTCTGGGGGAGGCGTGGTCCAGGCCGGGGCATCCCTGAGAGTCTCCTGTGCAG
CATCTGGATTCAGTTTGACTAGCTATGGGATGCACTGGGTCCGCCAGGCTCCAGGCAAGGGACTGGAGTG
GGTGGCTTTTATTTCGTCTGATGGTAGTGATAAGTACTATGTAGACTCTGTGAAGGGCCGATTCACCATC
TCCAGAGACACTTCCAAGAACATGATGTATCTGCAAATGAACAGCCTGACAACTGAGGATACGGCTGTGT
ATTACTGTGCGAAAGACTGGGGCAGCAACTGGTACCTCTTTGACTACTGGGGCCAGGGAACCCTGGTCAC
CGTCTCCTCAGGTGGAGGCGGTTCAGGCGGAGGTGGCTCTGGCGGTGGCGGATCGGACATCCAGATGACC
CAGTCTCCTTCCACCCTGTCTGCAGCTGTAGGAGACACAATCACCATTACTTGTCGGGCGAGTCAAGATT
TCAGGAACTGGTTAGCCTGGTATCAGCTGAAACCAGGAAAAGCCCCCAAGCCCCTGATCTATGGTGCATC
CACTTTGCAACATGGGGTCCCATCCAGGTTCAGCGGCAGTGGGTCTGGGACAGATTTCTCTCTCACTATC
AGTAGCCTGCAGCCTGAGGATTTTGCAACTTACTTTTGTCAACAGGCTCACAGTTTCCCTCCCACTTTCG
GCGGAGGGACCAAGCTGGAGATCAAACGT   (SEQ ID NO:3)

DNA Sequence with CDR Labels

CAGGTGCAGCTGGTGGAGTCTGGGGGAGGCGTGGTCCAGGCCGGGGCATCCCTGAGAGTCTCCTGTGCAG
          |----------CDR H1 (SEQ ID NO:19)--|
CATCTGGATTCAGTTTGACTAGCTATGGGATGCACTGGGTCCGCCAGGCTCCAGGCAAGGGACTGGAGTG
              |-----------------------CDR H2 (SEQ ID NO:20)--------------|
GGTGGCTTTTATTTCGTCTGATGGTAGTGATAAGTACTATGTAGACTCTGTGAAGGGCCGATTCACCATC

TCCAGAGACACTTCCAAGAACATGATGTATCTGCAAATGAACAGCCTGACAACTGAGGATACGGCTGTGT
            |-----------CDR H3 (SEQ ID NO:21)--|

FIGURE 5 - continued

```
ATTACTGTGCGAAAGACTGGGGCAGCAACTGGTACCTCTTTGACTACTGGGGCCAGGGAACCCTGGTCAC

CGTCTCCTCAGGTGGAGGCGGTTCAGGCGGAGGTGGCTCTGGCGGTGGCGGATCGGACATCCAGATGACC
                                                            |---------CDR L1
CAGTCTCCTTCCACCCTGTCTGCAGCTGTAGGAGACACAATCACCATTACTTGTCGGGCGAGTCAAGATT
(SEQ ID NO:22)                                                       |-------
TCAGGAACTGGTTAGCCTGGTATCAGCTGAAACCAGGAAAAGCCCCCAAGCCCCTGATCTATGGTGCATC
CDR L2-------(SEQ ID NO:23)
CACTTTGCAACATGGGGTCCCATCCAGGTTCAGCGGCAGTGGGTCTGGGACAGATTTCTCTCTCACTATC
                                                |---------CDR L3 (SEQ ID NO:24)
AGTAGCCTGCAGCCTGAGGATTTTGCAACTTACTTTTGTCAACAGGCTCACAGTTTCCCTCCCACTTTCG

GCGGAGGGACCAAGCTGGAGATCAAACGT (SEQ ID NO:3)
```

Amino Acid Sequence: 243 residues

```
QVQLVESGGGVVQAGASLRVSCAASGFSLTSYGMHWVRQAPGKGLEWVAFISSDGSDKYYVDSVKGRFTI
SRDTSKNMMYLQMNSLTTEDTAVYYCAKDWGSNWYLFDYWGQGTLVTVSSGGGGSGGGGSGGGGSDIQMT
QSPSTLSAAVGDTITITCRASQDFRNWLAWYQLKPGKAPKPLIYGASTLQHGVPSRFSGSGSGTDFSLTI
SSLQPEDFATYFCQQAHSFPPTFGGGTKLEIKR   (SEQ ID NO:4)
```

Amino Acid Sequence with CDR Labels

```
                           CDR H1(SEQ ID NO:25)           CDR H2(SEQ ID NO:26)
QVQLVESGGGVVQAGASLRVSCAASGFSLTSYGMHWVRQAPGKGLEWVAFISSDGSDKYYVDSVKGRFTI
                                   CDR H3 (SEQ ID NO:27)
SRDTSKNMMYLQMNSLTTEDTAVYYCAKDWGSNWYLFDYWGQGTLVTVSSGGGGSGGGGSGGGGSDIQMT
                       CDR L1(SEQ ID NO:28)    CDR L2 (SEQ ID NO:29)
QSPSTLSAAVGDTITITCRASQDFRNWLAWYQLKPGKAPKPLIYGASTLQHGVPSRFSGSGSGTDFSLTI
                   CDR L3 (SEQ ID NO:30)
SSLQPEDFATYFCQQAHSFPPTFGGGTKLEIKR
```

Isolated CDRs:

▓ - identical    ▓ - Similar charge

```
            (SEQ ID NO:13)
              H1                H2(SEQ ID NO:14)    H3(SEQ ID NO:15)
scFv 15    F   WMT         I              Q      ---R-----
scFv 38    L   GMH         F              K      WGSNW LF
          (SEQ ID NO:25)  (SEQ ID NO:26)         (SEQ ID NO:27)
          (SEQ ID NO:16)  (SEQ ID NO:17)
              L1              L2          L3 (SEQ ID NO:18)
scFv 15   QGDSLRSY AS     QD KRPS       AWD S  A
scFv 38   RASQDFRN LA     GA TLQH       QAH F  T
          (SEQ ID NO:28)  (SEQ ID NO:29) (SEQ ID NO:30)
```

FIGURE 5 - continued

BLOOD-BRAIN BARRIER TARGETING ANTIBODIES

CROSS REFERENCE TO RELATED APPLICATIONS

This application claims the benefit of U.S. Provisional Patent Application 61/925,809 filed Jan. 10, 2014, incorporated by reference herein.

STATEMENT REGARDING FEDERALLY SPONSORED RESEARCH/DEVELOPMENT

This invention was made with government support under NS071513 awarded by the National Institutes of Health. The government has certain rights in the invention.

BACKGROUND

The vascular network of the brain forms a biological barrier known as the blood-brain barrier (BBB). The BBB possesses a unique vascular phenotype that is induced by neighboring cells such as pericytes, astrocytes and neurons that together form the neurovascular unit (Abbott, N. J. and A. Friedman, Overview and introduction: The blood-brain barrier in health and disease. *Epilepsia,* 2012. 53: p. 1-6). This phenotype is best characterized as a combination of properties designed to maintain brain homeostasis, including tight paracellular junctions, a significant transporter repertoire, and a low basal level of pinocytosis, thereby rendering the BBB selectively permeable to required ions, nutrients and cells (Stutz, C., X. Zhang, and E. Shusta, Combinatorial Approaches for the Identification of Brain Drug Delivery Targets. *Curr. Pharm. Des.* 2013). While the BBB helps the brain to maintain the specific environment necessary for neuron function, it also prevents most small and large molecule therapeutics from gaining access to the brain (Jones, A. R. and Shusta, E. V., Blood-brain barrier transport of therapeutics via receptor-mediation; *Pharm. Res.,* 2007. 24(9): p. 1759-1771). The BBB is therefore a major impediment to the treatment of central nervous system disease, and effective delivery strategies remain scarce.

One promising delivery method involves targeting known receptor-mediated transport systems with antibodies to mediate non-invasive drug delivery past the BBB. Two prominent examples of this approach are antibodies that target the transferrin and insulin receptors (Pardridge, W. M., Y. S. Kang, and J. L. Buciak, Transport of Human Recombinant Brain-derived Neurotrophic Factor (BDNF) Through the Rat Blood-Brain Barrier in vivo Using Vector Mediated Peptide Drug Delivery; *Pharm. Res.,* 1994. 11(5): p. 738-746; Pardridge, W. M., Y. S. Kang, J. L. Buciak, and J. Yang, Human Insulin Receptor Monoclonal Antibody Undergoes High Affinity Binding to Human Brain Capillaries in vitro and Rapid Transcytosis Through the Blood-Brain Barrier in vivo in the Primate. *Pharm. Res.,* 1995. 12(6): p. 807-816). While these systems allow for therapeutic amounts of drug to penetrate the BBB, they are inherently non-selective and relatively inefficient. The current lack of brain drug delivery systems with ideal selectivity and efficiency has motivated the search for new antibodies capable of targeting and/or transporting therapeutic payloads into the brain (Stutz, C., X. Zhang, and E. Shusta, Combinatorial Approaches for the Identification of Brain Drug Delivery Targets. *Curr. Pharm. Des.* 2013).

To address this problem, one useful approach that has been employed is antibody-based screening. Such screens have been used to identify BBB cell surface proteins that can mediate brain targeting and, in some cases, transport. For instance, large combinatorial antibody libraries have been screened against brain endothelial cells in various formats, in vitro or in vivo, to discover both antibody targeting molecules and cognate brain endothelial cell proteins. While the identified antibody-BBB antigen pairs look promising for circumventing the BBB, in some cases only a handful of new antibodies have been isolated (Muruganandam, A., J. Tanha, et al., Selection of Phage-displayed Llama Single-Domain Antibodies That Transmigrate Across Human Bloodbrain Barrier Endothelium; *FASEB J.,* 2001. 15(14): p. 240). However, multiple genomic and proteomic studies support substantial differences in gene expression between the brain microvascular endothelium and the peripheral microvasculature, particularly in areas of transport and signaling between the brain and bloodstream (Li, J. Y., R. J. Boado, and W. M. Pardridge, Blood-brain Barrier Genomics, *J. Cereb. Blood Flow Metab.,* 2001. 21(1): p. 61-68; Calabria, A. R. and E. V. Shusta, Blood-brain Barrier Genomics and Proteomics: Elucidating Phenotype, Identifying Disease Targets and Enabling Brain Drug Delivery, *Drug Discov. Today,* 2006. 11(17-18): p. 792-799; Daneman, R., L. Zhou, D. Agalliu, J. D. Cahoy, et al., The Mouse Blood-Brain Barrier Transcriptome: A New Resource for Understanding the Development and Function of Brain Endothelial Cells. *PLoS One,* 2010. 5(10)).

Needed in the art is an improved BBB-selective antibody.

SUMMARY OF THE INVENTION

In one embodiment the present invention is a BBB-selective antibody, preferably comprising a protein encoded by SEQ ID NO:1 or 3. In another embodiment of the invention, the antibody comprises a peptide encoded by CDR H1, CDR H2, CDR H3, CDRL1, CDRL2 or CDRL3 of SEQ ID NO:1 or CDR H1, CDR H2, CDR H3, CDRL1, CDRL2, or CDRL3 of SEQ ID NO: 3.

In another embodiment of the present invention, the antibody is engrafted within a full IgG scaffold of human or other species origin or another scFv scaffold of human or other species of origin. In another embodiment, the BBB-selective antibody is connected to a compound, preferably a pharmaceutical or therapeutic compound.

In another embodiment, the invention is a vector comprising a BBB-selective antibody. In another embodiment, the invention is a microorganism comprising the vector. In another embodiment, the invention is a method of targeting a pharmaceutical or therapeutic compound to the blood brain barrier of a subject comprising the steps of obtaining a BBB-selective antibody attached to a pharmaceutical or therapeutic compound and exposing the antibody of step (a) to a subject's brain.

DESCRIPTION OF DRAWINGS

This patent application file contains at least one drawing executed in color. Copies of this patent or patent application publication with color drawings will be provided by the Office upon request and payment of the necessary fee.

FIG. 5 discloses the sequence of scFv15 and scFv38.

DESCRIPTION OF THE INVENTION

In General

Figure 1:
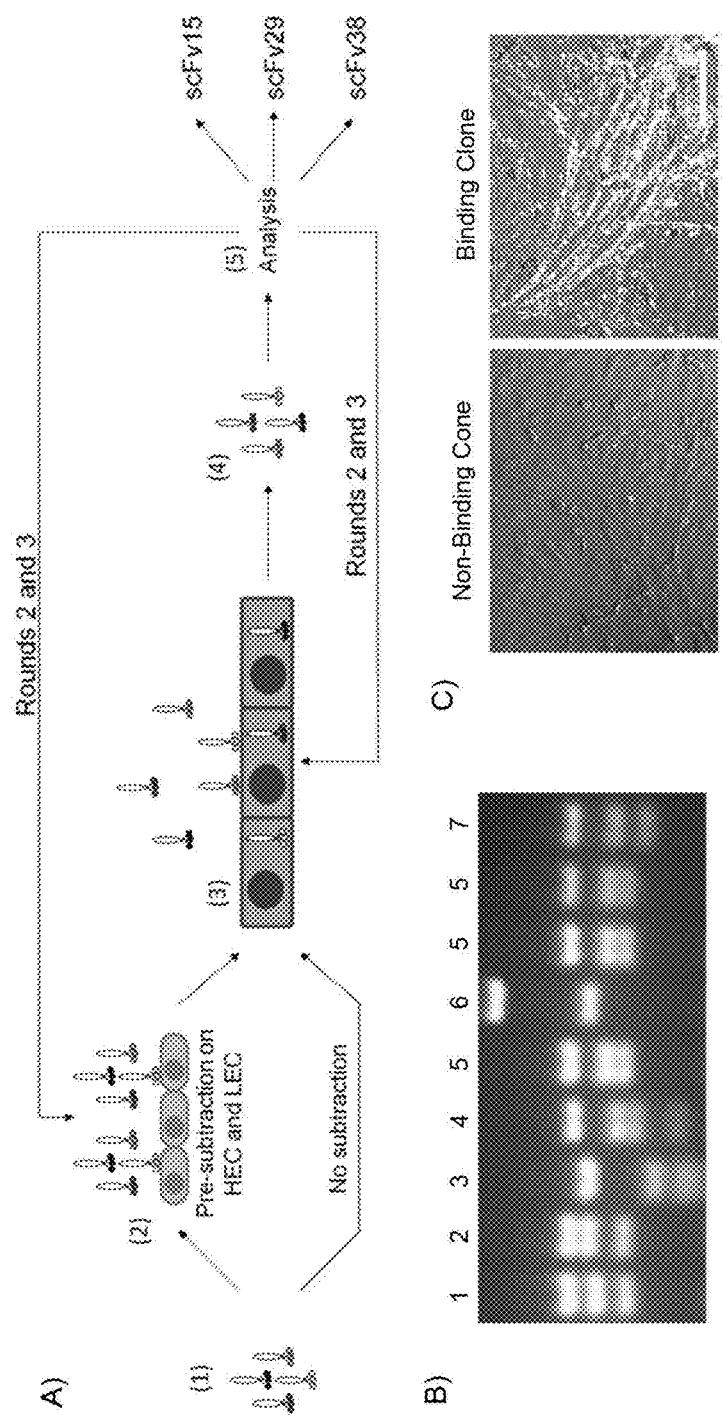
FIG. 1 (A-C) discloses antibody library screening on in vitro BBB model. A) Step 1: Display of a library of human scFv on fd-tet phage. Step 2: One path employed pre-subtraction techniques using rat heart (HEC) and rat lung (LEC) endothelial cell lines in an attempt to promote brain specificity. The parallel screening path did not employ library subtraction. Step 3: Library incubation with BMECs to allow for binding and internalization of the antibody bearing phage. Following incubation, the BMECs were washed and stripped. Step 4: The BMECs were lysed to recover the phage still associated with the cells because of internalization or stripping-resistant binding. Step 5: Library pools were analyzed on a clonal basis by phage titer, BstNI restriction mapping, and in the final rounds, phage immunocytochemistry. B) Sample BstN1 digestion pattern on an agarose gel. Patterns are categorized by number to indicate the clustering used to compile the statistics reported in Table 1. C) Sample images from clonal phage immunocytochemistry using BMECs to determine which clones displayed a binding phenotype. Image on left is a non-binding clone, and image on right is scFv38 in phage format. Scale bar is 50 μm.

In brief, and as discussed above, the blood-brain barrier (BBB) represents an obstacle in targeting and delivering therapeutics to the central nervous system. In order to discover new BBB targeting molecules, we panned a phage-displayed non-immune human single-chain antibody fragment (scFv) library against a representative BBB model comprised of hydrocortisone treated primary rat brain endothelial cells to obtain antibody fragments that target the BBB. As described below in the Examples, parallel screens were performed with or without pre-subtraction against primary rat heart and lung endothelial cells in an effort to identify antibodies that may have binding selectivity towards brain endothelial cells.

After three rounds of screening, we identified three unique scFvs (scFv15, scFv38, and scFv29) that maintained binding to primary rat brain endothelial cells, both in phage and soluble scFv format. While scFv29 and to a lesser extent, scFv15, exhibited brain endothelial cell selectivity in tissue culture, scFv29 did not appear to bind a BBB antigen in vivo. In contrast, both scFv15 and scFv38 demonstrated selective binding to rat brain vessels in vivo with substantial brain vascular selectivity as judged by differential vascular immune-labeling in tissue sections. scFv15 (SEQ ID NOS:1 and 2) and scFv38 (SEQ ID NOS:3 and 4) represent two new antibodies that are capable of binding antigens that are expressed at the BBB in vivo.

BBB-Selective Antibodies of the Present Invention

In one embodiment, the present invention is an antibody capable of selectively targeting the BBB. By "selectively" we mean the antibody is capable of binding to the surface of brain vessels but does not bind to lung, liver, or kidney tissue vasculature. By binding, we mean that the antibodies are capable of detection at a given tissue's endothelium by standard methods (eg. tissue section immunofluorescence assays.) By "antibody" we mean to include single chain antibodies, such as scFv15 and scFv38, and antibody fragments, such as the CDR segments within scFv15 and scFv38.

In one exemplary embodiment, the invention is a BBB-selective antibody comprising a sequence presented in FIG. 5. For example, the invention may be an expression vector that includes a polynucleotide encoding scFv15 or scFv38, such as the polynucleotide sequences set forth in SEQ ID NOs:1 or 3 or other degenerate tricodons that yield the same amino acid sequence. In other embodiments, the nucleotide or protein sequence comprises conservative or inconsequential substitutions or deletions. In other embodiments, the BBB-selective antibody is at least one of the complementarity determining region(s) (CDR) sequences disclosed in FIG. 5. Note that FIG. 5 discloses the CDRs in SEQ ID NOs: 1 and 3.

One may wish to engraft one or more CDRs from scFv15 or scFv38, the entire scFv, or fragments of the scFv into alternate scaffolds. For example, standard molecular biological techniques can be used to transfer the DNA sequences encoding the antibody's CDR(s) or scFv to (1) full IgG scaffold of human or other species origin; (2) another scFv scaffold of human or other species of origin or (3) other specialty vectors. If the CDR(s) have been transferred to a new scaffold all of the previous modifications described can also be performed. For example, one could consult *Biotechnol Genet Eng Rev,* 2013, 29:175-86 for a review of useful methods.

In other embodiments, the invention includes a purified and isolated host cell comprising an expression vector containing an isolated nucleic acid capable of encoding a BBB-selective antibody, such as the amino acid sequence set forth in any one of SEQ ID NOs:2 or 4. It should be appreciated that the host cell can be any cell capable of expressing antibodies, for example fungi; mammalian cells, including the Chinese hamster ovary cells; insect cells, using, for example, a baculovirus expression system; plant cells, such as, for example, corn, rice, *Arabidopsis*, and the like. See, generally, Verma, R. et al., *J Immunol Methods.* 1998 Jul. 1; 216(1-2):165-81.

Method of Transcytosis Across the BBB

Based upon the disclosed antibodies, the invention also contemplates a method of delivering a pharmaceutically active or otherwise therapeutic compound to and/or across the blood-brain barrier into a subject's brain. Such a method includes administering a pharmaceutically active or therapeutic compound in combination with a purified BBB-targeting antibody (e.g. scFv15 or scFv38) to a subject such that the antibody directs delivery of the pharmaceutically active or therapeutic compound to and/or across the blood brain barrier into the subject's brain.

Linkage of BBB-targeting antibodies of the present invention to pharmacologically active or therapeutic components.

In general, methods of conjugating, linking and coupling antibodies to pharmacologically active compounds are well known in the field. For example, see, Wu A M, Senter P D, Arming antibodies: prospects and challenges for immunoconjugates, *Nat Biotechnol.* 2005 September; 23(9):1137-46 and Trail P A, King H D, Dubowchik G M, Monoclonal antibody drug immunoconjugates for targeted treatment of cancer, *Cancer Immunol Immunother.* 2003 May; 52(5):328-37; Saito G, Swanson J A, Lee K D. Drug delivery strategy utilizing conjugation via reversible disulfide linkages: role and site of cellular reducing activities, *Adv Drug Deliv Rev.* 2003 Feb. 10; 55(2):199-215.

As well, the BBB-targeting antibodies may be provided in combination with liposome, nanoparticles or other analogous carriers loaded with a pharmaceutically active compound. Methods of preparing such compositions are known in the field (see, for example, Sugano et al., Antibody Targeting of Doxorubicin-loaded Liposomes Suppresses the Growth and Metastatic Spread of Established Human Lung Tumor Xenografts in Severe Combined Immunodeficient Mice *Cancer Research* 60, 6942-6949, Dec. 15, 2000 and Martin et al., Nanomaterials in Analytical Chemistry, *Analytical Chemistry News & Features,* May 1, 1998; pp. 322 A-327 A). As used herein, the phrase "antibody in combination with a pharmaceutically active compound" shall not be limited by the method of manufacture and such compositions may be produced by, but not limited to, techniques of conjugating, linking, coupling and decorating known in the art.

The following is a prophetic description of covalent chemical linkage of a proposed BBB-selective antibody to a pharmacologically active or therapeutic compound:

One may wish to link the antibodies of the present invention and active compounds via primary amines, for example as taken from Jones, A. R. and E. V. Shusta, Blood-brain barrier transport of therapeutics via receptor-mediation. *Pharmaceutical Research,* 2007. 24(9): p. 1759-1771. Lysine residues of either targeting vector (the scFv sequences) or protein therapeutic would be functionalized using Traut's reagent (2-iminothiolane.HCL) yielding a thiol. The thiol group, now attached to the lysine residue, is reacted with a maleimide-functionalized drug or vector resulting in a stable thio-ether bond. (One may or may not use a chemical spacer such as poly-ethylene glycol to reduce steric hindrance).

One may wish to use non-covalent linkage of the proposed antibody to pharmacologically active component. For example, one could use biotin/streptavidin interaction, such as the disclosure taken from Jones, A. R. and E. V. Shusta, Blood-brain barrier transport of therapeutics via receptor-mediation. *Pharmaceutical Research,* 2007. 24(9): p. 1759-1771.

Lysine residues of either the targeting vector or the protein therapeutic would be biotinylated using one of a number of commercial methods (such as N-hydroxysuccinimide biotin analogs). Then, either the vector or the therapeutic (whichever one was not modified in the previous step) would be conjugated to streptavidin or one of its variants (e.g., neutravidin) using one of the other methods presented here. The monobiotinylated reagent and the streptavidin conjugated counterpart would be combined and the near-covalent binding affinity would keep the reagents together.

One may wish to express BBB-targeted antibody as a fusion protein with a pharmacologically or therapeutically relevant peptide. For example, one may wish to express a scFv of the present invention with a protein linker and a protein therapeutic. Standard molecular biology techniques (e.g., restriction enzyme based subcloning, or homology based subcloning) could be used to place the DNA sequence encoding a protein therapeutic in frame with the targeting vector (usually a protein linker is also added to avoid steric hindrance). The fusion protein is then produced as one peptide in a host cell (e.g., yeast, bacteria, insect, or mammalian cell) and purified before use. Note the therapeutic does not need to be a whole protein. (I.e., It can be a single peptide chain as a subunit in a protein with more than one peptide. The other peptides can be co-expressed with the vector fusion and allowed to associate in the host cell or after secretion).

The three methods of linkage described above can also be used in the same manner to conjugate the BBB-targeting antibody to therapeutic compounds, such as compounds that are useful in disease/illness prevention, cure or alleviation. Therapeutic compounds include compounds such as a fluorophore, dye, or other marker for use as diagnostic tool.

We also include large particles as "therapeutic" compounds. For example, one may wish to decorate liposomes or nanoparticles with an embodiment of the targeting vector. Preferably, procedures to create vector-decorated liposomes may be taken from Jones, A. R. and E. V. Shusta, Blood-brain barrier transport of therapeutics via receptor-mediation. *Pharmaceutical Research,* 2007. 24(9): p. 1759-1771. Liposomes may be created using phospholipids, one of which is poly-ethylene glycol-distearoylphosphatidylethanolamine (PEG-DSPE) functionalized with maleimide as in the chemical linkage described above. The liposomes can be created such that they encapsulate a therapeutic in the lipid-based sphere. The vector may be modified using Traut's reagent and attached to the surface of the liposome as described in the chemical linkage methods. Note: Nanoparticles can be treated in the same way, except that the particles are solid-based (e.g., poly-butylcyanoacrylate) and must be artificially PEGylated before reaction with modified vectors.

Administration of Antibodies with or without Above Modifications

One may wish to administer the BBB-selective antibodies of the present invention without the modifications described above. For example, one may administer the antibodies through an intravenous injection or through intra-peritoneal and subcutaneous methods.

Examples

In General

The blood-brain barrier (BBB) represents an obstacle in targeting and delivering therapeutics to the central nervous system. In order to discover new BBB targeting molecules, we panned a phage-displayed non-immune human single-chain antibody fragment (scFv) library against a representative BBB model comprised of hydrocortisone-treated primary rat brain endothelial cells. Parallel screens were performed with or without pre-subtraction against primary rat heart and lung endothelial cells in an effort to identify antibodies that may have binding selectivity towards brain endothelial cells. After three rounds of screening, three unique scFvs (scFv15, scFv38, and scFv29) were identified that maintained binding to primary rat brain endothelial cells, both in phage and soluble scFv format. While scFv29 and to a lesser extent, scFv15, exhibited some brain endothelial cell specificity in tissue culture, scFv29 did not appear to bind a BBB antigen in vivo. In contrast, both scFv15 and scFv38 were capable of immune-labeling rat brain vessels in vivo and displayed brain vascular selectivity with respect to all peripheral organs tested other than heart. Taken together, scFv15 and scFv38 represent two new antibodies that are capable of binding antigens that are expressed at the BBB in vivo.

Introduction

The vascular network of the brain forms a biological barrier known as the blood-brain barrier (BBB). The BBB possesses a unique vascular phenotype that is induced by neighboring cells such as pericytes, astrocytes and neurons that together form the neurovascular unit [Abbott, N.J. and A. Friedman, Overview and introduction: The blood-brain barrier in health and disease. Epilepsia, 2012. 53: p. 1-6.] This phenotype is best characterized as a combination of properties designed to maintain brain homeostasis, including tight paracellular junctions, a significant transporter repertoire, and a low basal level of pinocytosis, thereby rendering the BBB selectively permeable to required ions, nutrients and cells [Stutz, C., X. Zhang, and E. Shusta, Combinatorial Approaches for the Identification of Brain Drug Delivery Targets. Curr. Pharm. Des. 2013, DOI: 10.2174/13816128113199990459]. While the BBB helps the brain to maintain the specific environment necessary for neuron function, it also prevents most small and large molecule therapeutics from gaining access to the brain [Jones, A. R. and E. V. Shusta, Blood-brain barrier transport of therapeutics via receptor-mediation. Pharm. Res., 2007. 24(9): p. 1759-1771].

The BBB is therefore a major impediment to the treatment of central nervous system disease, and effective delivery strategies remain scarce. One promising delivery method involves targeting known receptor-mediated transport systems with antibodies to mediate non-invasive drug delivery past the BBB. Two prominent examples of this approach are antibodies that target the transferrin and insulin receptors [Pardridge, W. M., Y. S. Kang, and J. L. Buciak, Transport of human recombinant brain-derived neurotrophic factor (BDNF) through the rat blood-brain barrier in vivo using vector mediated pepted drug delivery. Pharm. Res., 1994. 11(5): p. 738-746.5. Pardridge, W. M., Y. S. Kang, J. L. Buciak, and J. Yang, Human insulin receptor monoclonal antibody undergoes high affinity binding to human brain capillaries in vitro and rapid transcytosis through the blood-brain barrier in vivo in the primate. Pharm. Res., 1995. 12(6): p. 807-816]. While these systems allow for therapeutic amounts of drug to penetrate the BBB, they are inherently non-specific and relatively inefficient. The current lack of brain drug delivery systems with ideal specificity and efficiency has motivated the search for new antibodies capable of targeting and/or transporting therapeutic payloads into the brain [Stutz, C., et al., 2013, supra].

To address this problem, one useful approach that has been employed is antibody-based screening. Such screens have been used to identify BBB cell surface proteins that can mediate brain targeting and, in some cases, transport. For instance, large combinatorial antibody libraries have been screened against brain endothelial cells in various formats, in vitro or in vivo, to discover both antibody targeting molecules and cognate brain endothelial cell proteins [Calabria, A. R. and E. V. Shusta, A genomic comparison of in vivo and in vitro brain microvascular endothelial cells. J. of Cereb. Blood Flow Metab., 2008. 28(1): p. 135-148; Shusta, E. V., R. J. Boado, G. W. Mathern, and W. M. Pardridge, Vascular genomics of the human brain. J. of Cereb. Blood Flow Metab., 2002. 22(3): p. 245-252; Li, J. Y., R. J. Boado, and W. M. Pardridge, Blood-brain barrier genomics. J. Cereb. Blood Flow Metab., 2001. 21(1): p. 61-68; Li, J. Y., R. J. Boado, and W. M. Pardridge, Rat blood-brain barrier genomics. II. J. Cereb. Blood Flow Metab., 2002. 22(11): p. 1319-1326]. While, in some cases, the identified antibody-BBB antigen pairs look promising for circumventing the BBB [Muruganandam, A., J. Tanha, S. Narang, and D. Stanimirovic, Selection of phage-displayed llama single-domain antibodies that transmigrate across human blood-brain barrier endothelium. FASEB J., 2001. 15(14): p. 240-+], only a handful of new antibodies have been isolated [Stutz, C., et al., 2013, supra]. However, multiple genomic and proteomic studies support substantial differences in gene expression between the brain microvascular endothelium and the peripheral microvasculature, particularly in areas of transport and signaling between the brain and bloodstream [Li, J. Y., R. J. Boado, and W. M. Pardridge, Blood-brain barrier genomics. J. Cereb. Blood Flow Metab., 2001. 21(1): p. 61-68; Calabria, A. R. and E. V. Shusta, Blood-brain barrier genomics and proteomics: elucidating phenotype, identifying disease targets and enabling brain drug delivery. Drug Discov. Today, 2006. 11(17-18): p. 792-799; Daneman, R., L. Zhou, D. Agalliu, J. D. Cahoy, et al., The Mouse Blood-Brain Barrier Transcriptome: A New Resource for Understanding the Development and Function of Brain Endothelial Cells. PLoS One, 2010. 5(10)], Thus, in order to access the unexplored BBB proteome and expand the repertoire of BBB targeting antibodies, we panned a large phage-displayed library of nonimmune human scFv on an in vitro BBB model based on primary rat brain endothelial cells that are capable of mimicking key BBB characteristics such as elevated trans-endothelial electrical resistance, improved tight junction integrity, and a molecular signature that moves towards the in vivo BBB [Calabria, A. R. and E. V. Shusta, 2008, supra; Calabria, A. R., C. Weidenfeller, A. R. Jones, H. E. de Vries, et al., Puromycin-purified rat brain microvascular endothelial cell cultures exhibit improved barrier properties in response to glucocorticoid induction. J. Neurochem., 2006. 97(4): p. 922-933]. Because of the aforementioned interest in antibodies that may be selective towards the BBB and/or mediate BBB internalization, our screen employed phage subtraction and internalization approaches. Three particularly interesting scFvs were isolated from the screen, with two that were subsequently shown to preferentially bind to the rat brain microvasculature in vivo.

Materials and Methods

Cell Isolation and Culture

The brain microvascular endothelial cell (BMEC) isolation was performed as previously described [Calabria, A. R., C. Weidenfeller, et al., 2006, supra]. The purified BMECs were plated on collagen type IV and fibronectin (Sigma-Aldrich, # C5533 and # F1141) coated tissue culture plates and cultured in endothelial cell culture medium consisting of DMEM supplemented with 20% platelet-poor bovine plasma derived serum (PDS, from Biomedical Technologies, # BT-214), heparin at 1 µg/mL (Sigma-Aldrich, # H3393), L-glutamine at 2 mM (Sigma-Aldrich, # G8540), 100× Antibiotic-Antimycotic (Life Technologies, #15240-062), and basic fibroblast growth factor at 1 ng/mL (bFGF, R&D Systems, #233-FB). For the first two days of culture, the medium also included 4 µg/mL of puromycin (Sigma-Aldrich, # P8833) for BMEC purification purposes. Upon reaching confluence, BBB properties were induced by changing to serum-free medium consisting of 50% DMEM and 50% Ham's F-12 (Life Technologies, #11765-054) with L-glutamine at 2 mM and Antibiotic-Antimycotic supplemented with 550 nM hydrocortisone for 24 hours before use.

The primary rat heart and lung microvascular endothelial cells (HEC/LEC) were obtained from VEC Technologies (Rensselaer, N.Y.), and cultured per manufacturer's instructions on fibronectin coated tissue culture plates in MCDB-131 complete medium (VEC technologies).

Screening on BMECs

All of the screening methods are based on protocols outlined in Zhou and Marks [Zhou, Y. and J. D. Marks, Identification of target and function specific antibodies for effective drug delivery, in: Therapeutic Antibodies: Methods and Protocols, A. Dimitrov, Editor. 2009, Humana Press: Totowa. p. 145-160]. Before screening for phage internalization on BMECs, the human scFv displaying Fd-tet library [Sheets, M. D., P. Amersdorfer, R. Finnern, P. Sargent, et al., Efficient construction of a large nonimmune phage antibody library: The production of high-affinity human single-chain antibodies to protein antigens. Proc. Natl. Acad. Sci. USA, 1998. 95(11):p. 6157-6162; O'Connell, D., B. Becerril, A. Roy-Burman, M. Daws, et al., Phage versus phagemid libraries for generation of human monoclonal antibodies. J. Mol. Bio., 2002. 321(1): p. 49-56] was first pre-subtracted for common endothelial antigens by serially applying the library to T-75 flasks of HEC and LEC. Culture medium for all cells was replaced with 3 mL of MCDB-131 complete medium for HEC and LEC, and 20 mL of serum-free medium with hydrocortisone for BMECs, 1 hour before use. For the first round, $2 \times 10^{11}$ colony forming units (cfu) of the scFv library were added to a flask of LECs containing 3 mL of MCDB-131 complete media and incubated for 1 hour at room temperature. MCDB-131 complete medium from the HECs was removed and replaced with the phage containing MCDB-131 complete medium from the LEC flask and incubated at room temperature for another hour. The serum free medium with hydrocortisone from the BMEC T-75 flask was then removed and replaced with the medium from the HEC flask containing the now pre-subtracted library. In parallel, $2 \times 10^{11}$ cfu of the Fd-tet library were added to a separate T-75 flask of BMECs containing 3 mL of serum free medium for the non-subtracted screen. The BMEC flasks were kept at 4° C. for 1 hour and rocked for 5 minutes every half-hour to encourage phage binding. The flasks were then washed quickly with 1 mL of phosphate buffered saline (PBS, 137 mM sodium chloride, 2.7 mM potassium chloride, 10 mM dibasic sodium phosphate, 1.8 mM monobasic potassium phosphate, pH 7.4) five times. Three mL of pre-warmed serum free medium was added to the BMECs and the flasks were moved to an incubator at 37° C. and 5% $CO_2$ for 40 minutes and gently rocked several times to promote phage internalization. For rounds 2 and 3, the procedure described above was repeated except the BMEC flasks were washed 3 times with 25 mL of PBS, followed by addition of 20 mL of pre-warmed serum free medium supplemented with hydrocortisone, prior to incubation at 37° C. for 15 minutes.

After round 1, BMECs were washed three times with 1 mL ice cold PBS. Subsequent rounds were washed three times with 10 mL of PBS. The loosely bound phage were stripped from the surface of the cells by adding of 4 mL stripping buffer I (500 mM sodium chloride, 0.2 M urea, 2 mg/mL polyvinylpyrrolidone in 50 mM glycine, pH 2.8) three times at room temperature for 5 minutes. The stripping buffer fractions were recovered and neutralized with 2 mL of 1 M Tris-HCL (pH 7.4), then placed on ice, and reserved for titering and storage. The still-adherent cells were washed two times in 10 mL of PBS at room temperature and then once with 2 mL of 0.25% trypsin/EDTA (Life Technologies, #25200-056). Then, 2 mL of fresh trypsin/EDTA was added to the BMECs and incubated at 37° C. for no longer than 10 minutes to detach the cells and further remove phage bound to the outside of the BMEC. The detached cells were moved to a conical tube and centrifuged at 300 g at 4° C. for 5 minutes. The cell pellet was then washed twice with 10 mL ice cold hydrocortisone supplemented serum free medium and then re-suspended in 1 mL of ice cold lysis Buffer (100 mM triethanolamine in $ddH_2O$), triturated, and incubated on ice for 10 minutes. The lysate containing the "cell-associated fraction" was neutralized by triturating with 0.5 mL of 1 M Tris-HCL (pH 7.4).

The phage were recovered from the cell-associated fraction by incubation with an excess of log phase TG1 *Escherichia coli* cells from Agilent Technologies (Santa Clara, Calif.). Briefly, 0.75 mL of phage-containing fractions were added to 10 mL of log phase TG1 *E. coli* and incubated at 37° C. for 30 minutes, followed by another 30 minute incubation at 37° C. while shaking. A volume of 300 µL of the phage bearing TG1 was used for titer determination. The rest was plated on two 150 mm 2×YT (16 g/L Bacto Tryptone, 10 g/L Bacto Yeast Extract, and 5 g/L sodium chloride, pH 7.0) agar plates with 15 µg/mL tetracycline and incubated at 37° C. overnight. The phage-harboring bacteria were subsequently scraped off the plates using 2×YT medium, expanded in 200 mL culture and phage in the culture supernatant was recovered by standard polyethylene glycol (PEG) precipitation [Zhou, Y. and J. D. Marks, 2009, supra]. For subsequent screening rounds, $1 \times 10^{11}$ cfu of phage from the cell-associated fraction were used, except for round 2 of the pre-subtracted library screen. The recovery of phage from round 1 in this pool was lower than expected, so round 2 of the pre-subtracted screen was treated the same way as round 1 (using less stringent conditions than round 2 for the non-subtracted pool) except phage was applied in a ratio of 5:1 of cell-associated fraction to third stripping fraction, and stripping buffer II (150 nM sodium chloride, 100 mM glycine, pH 2.5) was used in place of stripping buffer I.

DNA Fingerprinting by BstN1 Digestion

Estimates of post-screen pool diversity were determined by BstN1 digestion of scFv-encoding inserts. Briefly, bacteria infected from phages isolated from the post-screen pools were spread on TYE (10 g/L bacto tryptone, 15 g/L bacto yeast extract, and 8 g/L sodium chloride, pH to 7.0) agar plates with 15 μg/mL tetracycline and allowed to grow overnight at 37° C. into isolated colonies. Ninety-six of these were picked off the plate, expanded, and stored in 15% glycerol at −80° C. until experiment was performed. Whole cell PCR was performed using Platinum® Taq (Life Technologies, #10966-034) per manufacturer's instructions on each of the wells described above using primers that flank the scFv gene in the phage DNA. The primer sequences were 5'-TTTTTGGAGATTTTCAACGTGA-3' (SEQ ID NO:5), and 5'-GAATTTTCTGTATGAGGTTTTGCTAAA-3 (SEQ ID NO:6)' for the forward and reverse primers, respectively. The PCR product was then digested with the restriction enzyme BstN1 (New England Biolabs # R0168L) per manufacturer's instructions. The digestion products were run on a 3% agarose gel, stained with ethidium bromide and imaged using the Molecular Imager Gel Doc XR System from Bio-Rad (Hercules, Calif.). The resulting images were analyzed for distinct patterns in each lane and categorized accordingly.

Enzyme Linked Immunosorbent Assay (ELISA) for Phage Binding

BMECs were cultured in 96 well tissue culture plates as described above. The day of the assay, each well of BMECs was blocked with 250 μL of PBSCM (PBS with 1 mM of calcium chloride and 0.5 mM of magnesium sulfate) supplemented with 40% goat serum (PBSCMG) (Sigma-Aldrich, #G6767). The wells were washed three times with 250 μL of PBSCM. Overnight cultures of phage-harboring bacteria were centrifuged, and 50 μL of the phage-containing supernatant from each sample was incubated directly on the BMECs in the presence of 100 μL of fresh PBSCMG. The plate was incubated for one hour at 4° C. and then washed once. An anti-M13-HRP antibody (GE Healthcare, #27942101) diluted 1:500 in PBSCMG was incubated in each well for one hour at 4° C. Following this, the cells were washed three times in PBSCM and a colorimetric substrate was added to each well and incubated for 30 minutes (ABTS (Sigma-Aldrich, # A9941) prepared by manufacturer's instructions). The plate was then read at 405 nm using an EL800 Universal Microplate Reader from BioTek (Winooski, Vt.).

Preparation of Soluble Hexahistidine-Tagged scFv

The following method for secreting the soluble scFv-His6 fusion is based on a protocol described in Zhou and Marks [Zhou, Y. and J. D. Marks, 2009, supra]. An overnight bacterial culture harboring the scFv secretion plasmid was used to inoculate 2×YT medium containing 100 μg/mL ampicillin and 0.1% glucose, which was then grown at 37° C. until an $OD_{600\ nm}$ of 0.9 was reached. Expression was induced by adding 1 mM isopropyl-β-D-thiogalactopyranoside (IPTG, Fisher Scientific, #50213380) and the bacteria were allowed grow for 4 hours at 30° C. The bacteria were harvested and the scFv recovered by serial incubation with a periplasmic extraction buffer (PPB, 200 g/L sucrose, 1 mM EDTA, 30 mM tris-HCl, pH 8.0) supplemented with DNAse I (Roche Applied Sciences, #10104159001) to 100 μg/mL, and cOmplete™ Mini, protease inhibitor cocktail tablets, (Roche Applied Sciences, #11836153001) and an osmotic shock buffer (OSB, 5 mM magnesium sulfate in $ddH_2O$) supplemented with DNAse I and cOmplete™ Mini. The result was syringe filter sterilized, and dialyzed against PBS+10 mM imidazole. The scFv were purified from the crude extract with HisPur™ Ni-NTA spin columns (Thermo Scientific, #8224) using manufacturer recommended protocol for purification by gravity flow. The purified scFvs were eluted and subsequently dialyzed against PBS, and the purity of the scFv was verified by SDS polyacrylamide gel electrophoresis (SDS-PAGE) and Coomassie blue staining Finally, the elution fractions were sterile filtered using Ultrafree™ centrifugal filtration units (Millipore # UFC30GV25), and quantified using UV 280 nm absorbance and extinction coefficients generated by ExPASy (http://web.expasy.org/protparam/).

Immunocytochemical Labeling of Cultured Cells with Soluble scFv

BMEC, LEC, or HEC were cultured as described above. The cells were washed once with 300 μL ice cold PBSCM, blocked for 30 minutes on ice with 300 μL of PBSCMG. The cells were incubated with 300 μL of 100 μg/mL (~3 μM) scFv monomer in PBSCMG for 2.5 hours on ice. The cells were washed 2 times with ice cold PBSCM, and then the surface was labeled with 250 μL of a mouse anti-c-myc antibody (Covance # MMS-150P) at a 1:250 dilution in PBSCMG for 30 minutes on ice. This was followed by 2 washes in ice cold PBSCM and a 30 minute incubation with 250 μL of goat anti-mouse Alexa Fluor® 594 (Life Technologies #A11032) diluted 1:400 in PBSCMG. The nuclear stain, DAPI (Life Technologies, #D1306) was applied for 4 minutes at room temperature at a concentration of 300 nM in 300 μL of PBS, and then the cells were washed three times with ice cold PBSCM and post fixed for 8 minutes at room temperature with paraformaldehyde (4% w/v in PBS). Finally, the cells were washed three times in PBSCM, with 0.5 mL of wash buffer and visualized using an Olympus fluorescence microscope connected to a Diagnostic Instruments camera run by MetaVue.

ScFv internalization was also assayed using a procedure similar to above with the following modifications: The scFv were pre-dimerized with the mouse anti-c-myc antibody at a molecular ratio of 4 scFv to 1 anti-c-myc antibody in PBSCMG. The pre-dimerized scFv was incubated with BMECs for 1 hour on ice and then transferred to an incubator at 37° C. and 5% $CO_2$ for 30 minutes to allow for internalization. The cells were next incubated with Alexa Fluor® 594 as described previously. The cells were then fixed in paraformaldehyde for 8 minutes and washed 2 times in ice cold PBSCM. The cells were permeabilized using 0.6% Triton™ X-100 (Sigma-Aldrich, #X100) in PBSCMG for 30 minutes. Next, the cells were washed 2 times in ice cold PBSCM and incubated with goat anti-mouse Alexa Fluor® 488 (Life Technologies, #A11029) diluted 1:400 in PBSCMG. The cells were then labeled with DAPI, fixed again, and viewed under the fluorescent microscope as previously described. A positive control antibody against the rat transferrin receptor (AbD Serotec, # MCA155G) was used at a dilution of 1:200.

Flow Cytometric Analysis of Cultured Cells with Soluble scFv

BMEC, LEC, or HEC were cultured as described above. The cells ($2 \times 10^6$ cells/T-25 flask) were washed in PBS and detached from the T-25 culture flasks using 1 mL of Accutase™ (Life Technologies, # A11105-01). The cells were transferred to a conical tube, centrifuged at 800 g for 10 minutes, and resuspended in PBSG (PBS with 40% goat serum) and blocked on wet ice for 30 minutes. The cells from each flask were separated into 5 equal samples containing 4×10⁵ cells which were centrifuged and resuspended in 300 μL scFv monomer at 100 μg/mL (~3 μM) in PBSG and incubated for 60 minutes on ice. The cells were centrifuged as above and washed once in 1 mL of ice cold wash buffer (PBS with 5% goat serum) and centrifuged again. The samples were resuspended in mouse-anti-c-myc in 300 μL of PBSG at a 1:250 dilution and incubated on ice for 30 minutes. The cells were washed once in 1 mL of ice cold wash buffer, centrifuged and resuspended in a goat anti-mouse antibody conjugated to allophycocyanin (APC, Life Technologies, #A865) in 300 μL of PBSG and incubated for 30 minutes. The cells were washed two times and resuspended in flow buffer (PBS+0.1% BSA+5 mM EDTA) supplemented with Sytox® (Life Technologies, # S7020)) diluted 1:10,000 and analyzed on a flow cytometer (Becton Dickinson FACSCalibur™).

Immunohistochemical Labeling of Rat Tissue Sections with Soluble scFv

Rat brain, heart, lung, liver, and kidney were dissected from a male Sprague-Dawley rat, snap frozen, and 7 μM cryosections were prepared. Prior to use, the sections were removed from the freezer and allowed to thaw and air dry for approximately 20 minutes. The sections were wetted in sterile PBS at room temperature. Next, tissue sections were blocked in PBSG for 30 minutes. ScFv monomer was diluted to 100 μg/mL (~3 μM) in 300 μL, of PBSG and incubated on the tissue sections on ice for 2.5 hours (kidney used 50 μg/mL scFv). The sections were washed twice with ice cold PBS and the mouse anti-c-myc antibody diluted 1:250 in 300 μL, of PBSG was incubated on the sections for 30 minutes on ice. The sections were next washed twice and incubated with an Alexa Fluor® 594 conjugated anti-mouse antibody diluted 1:400 and isolectin B4 conjugated FITC (IB4-FITC, Sigma-Aldrich # L2895) diluted 1:100 in PBSG for 30 minutes. The samples were washed three times and fixed in 4% paraformaldehyde for 10 minutes at room temperature. Kidney sections serial to the scFv labeled sections were labeled in a similar manner but with an anti-rat CD31 antibody (Thermo Scientific, #MA1-81051) to visualize endothelial cells in place of the IB4-FITC. The sections were viewed using an Olympus fluorescence microscope connected to a Diagnostic Instruments camera run by Meta-Vue.

Results

Screening of Phage Display scFv Library on BMECs

The screen was performed using a rat in vitro BBB model described previously [Calabria, A. R., C. Weidenfeller, et al., 2006, supra]. The model employs primary rat brain microvascular endothelial cells (BMECs) that are purified by puromycin treatment, and after confluence, BBB properties are induced with hydrocortisone [Calabria, A. R., C. Weidenfeller, et al., 2006, supra]. This model was chosen as the cellular screening platform because hydrocortisone induction enhances the in vivo relevance of the model by leading to increases in trans-endothelial electrical resistance, improvements in tight junction morphology, and molecular changes that move the model more towards the in vivo situation [Calabria, A. R. and E. V. Shusta, 2008, supra; Calabria, A. R., C. Weidenfeller, et al., 2006, supra].

A library of 5×10⁸ human-derived scFvs displayed on the surface of Fd-tet phage [Sheets, M. D., et al., 1998; supra; O'Connell, D., B. Becerril, et al., 2002, supra] was panned against the BMECs. This library was chosen primarily for its multi-valent display of scFv (3-5 copies per phage) to help bias the screen towards antibodies capable of internalization [Poul, M. A., B. Becerril, U. B. Nielsen, P. Morisson, et al., Selection of tumorspecific internalizing human antibodies from phage libraries. J. Mol. Bio., 2000. 301(5): p. 1149-1161]. To this end, the screen was designed to enrich the recovered pools for internalized phages; but, as the data below indicate, the screen will also recover those antibody-bearing phage that bind well to the BMEC cell surface (FIG. 1A). Within this functional screen, one path incorporated a pre-subtraction step prior to each round of screening in which the phage libraries were first incubated successively on primary rat heart (HEC) and rat lung (LEC) endothelial cell lines prior to using the unbound phage for screening on BMECs (FIG. 1A, see Materials and Methods for details). The rationale was to attempt to remove phages that bind to common endothelial cell antigens and help promote brain selectivity. The parallel screening path did not employ subtraction in order to access the diversity of the entire antibody library and corresponding BMEC antigens. The pre-subtracted or non-subtracted phage pools were then incubated on hydrocortisone-induced BMECs grown in a tissue culture flask, first on ice as a binding step and then at 37° C. to allow for possible phage internalization. The surface of the BMECs was subsequently washed and stripped with a low pH buffer. After trypsinization and lysis, the phages that had either internalized or were incompletely stripped were recovered in TG1 E. Coli, titered and this cell-associated fraction was used for the next round of screening (Table 1). As one exception to this strategy, it was noted that the diversity of the cell-associated fraction resulting from round 1 of the pre-subtraction screen was quite low and thus for round 2 phage recovered in the last stripping wash were combined with the cell-associated fraction (Table 1). The screen progress was followed both by phage titer and by BstN1 restriction-based DNA fingerprinting (Table 1 and FIG. 1B). While the titer in the pre-subtracted screens continued to increase throughout three rounds of enrichment, by round 3 the diversity had been reduced to just two unique digestion patterns (Table 1). By contrast, the amount of phage recovered from the non-subtracted library increased from round 1 to round 2, but plateaued in round 3, and the diversity remained comparatively high. At this point, the scFv-bearing phages were analyzed on a clonal basis.

Clonal Assessment of Recovered scFvs

Antibody-bearing phage clones were individually assessed in a BMEC cell-based phage ELISA to determine those clones capable of binding BMECs. Out of 395 individual clones sampled from rounds 2 and 3 of the pre-subtracted and non-subtracted pools, 39 clones yielded an elevated ELISA signal. Evaluation of these clones based on BstN1 digestion patterns, reduced the number of potentially unique binding antibody-bearing phage clones to 22. Further evaluation of these 22 clones by phage-based immunocytochemistry revealed 10 phage clones with definitive binding to cultured BMECs (FIG. 1C). Sequencing of the 10 clones yielded three unique scFv sequences. One clone designated scFv38 appeared in both pre-subtracted and non-subtracted pools resulting from round 3 of screening, scFv29 was found in round 3 of the pre-subtracted pool, and scFv15 was found only in round 2 of the pre-subtracted pool.

Figure 2:
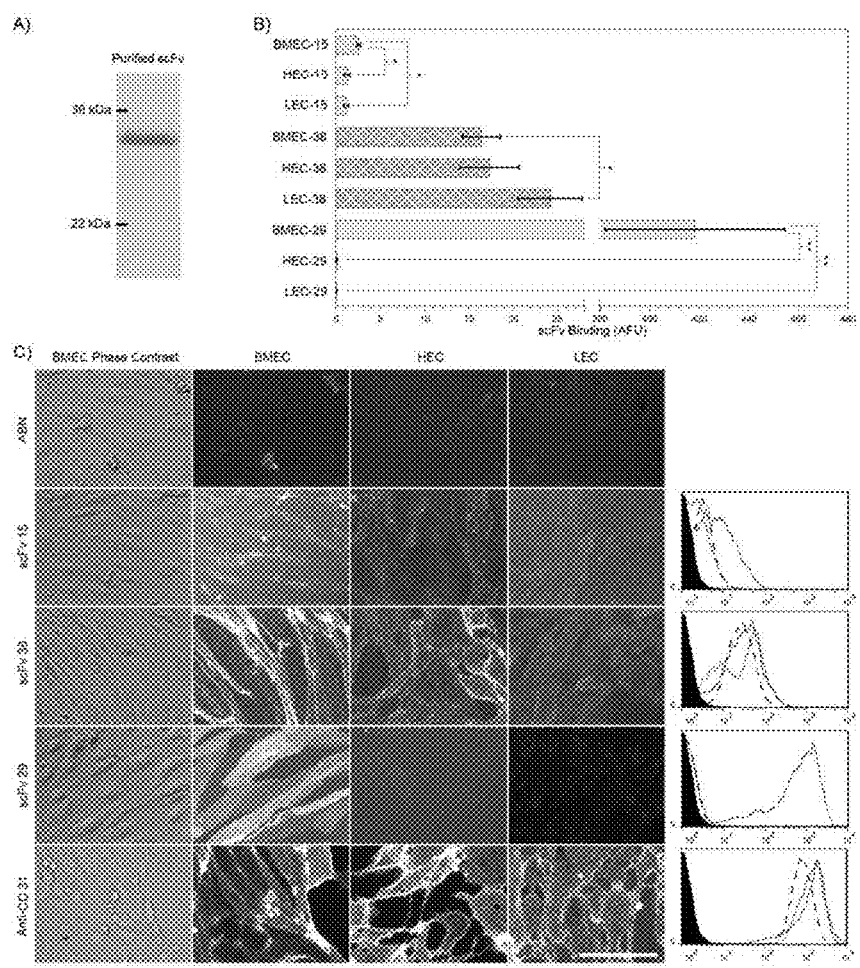
FIG. 2 (A-C) illustrates the production and assessment of soluble scFv binding profiles in cultured cells. A) Purified scFv electrophoresed on an SDS-PAGE gel stained with Coomassie blue. scFv38 is shown. B) Quantitative antibody binding resulting from flow cytometric analyses of scFv15, scFv38, and scFv29 on BMEC, HEC, and LEC. Experiments were performed on cells cultured in separate triplicate wells. Expressed are the specific signals after subtraction of the irrelevant, anti-botulinum (ABN) scFv background, mean±S.D. An asterisk represents p<0.05, and a double asterisk p<0.005 computed using a student's two-tailed t-test assuming unequal variances. C) Purified ABN scFv (negative control), scFv15, scFv38, and scFv29 scFv as well as anti-CD31 antibody (positive control) were incubated on BMECs, HECs, and LECs. The scFv immunolabeling concentration was 100 μg/ml (~3 μM) and is most likely saturating the targeted receptors. Scale bar is 50 μm. The histograms at the right of each row of images are sample flow cytometry histograms for each respective antibody, with quantified data in Panel B. The x-axis of the histograms represents antibody binding intensity in arbitrary fluorescent units. The filled line represents the ABN scFv negative control, the solid line is binding signal arising from BMEC, the dotted line is binding signal from HEC, and the dashed line is binding signal from LEC.

These three scFv were subcloned, expressed in bacteria and purified via a hexahistidine tag (FIG. 2A). Purified scFv were used to immunolabel BMECs, HECs, and LECs. Fluorescent microscopy and flow cytometry were used to assess their qualitative and quantitative BMEC binding specificity, respectively. ScFv29 originated from the pre-subtracted screens and exhibited very clear preferential binding to BMEC's without detectable binding to either the HECs or LECs (FIG. 2C), and this finding was corroborated by flow cytometry (FIGS. 2B and 2C). In contrast, scFv15, which also originated in the pre-subtracted pool, exhibited more limited binding to BMECs and also yielded detectable binding to HECs and LECs (FIG. 2B). While there was certainly less BMEC specificity for scFv15 compared with scFv29, flow cytometric quantification indicated that scFv15 binding to BMECs was increased compared with binding to either HECs or LECs (FIG. 2C, $p<0.05$). ScFv38 was found in both non-subtracted and pre-subtracted pools, and accordingly bound all three cell types with roughly the same intensity (FIGS. 2B and C).

Figure 3:
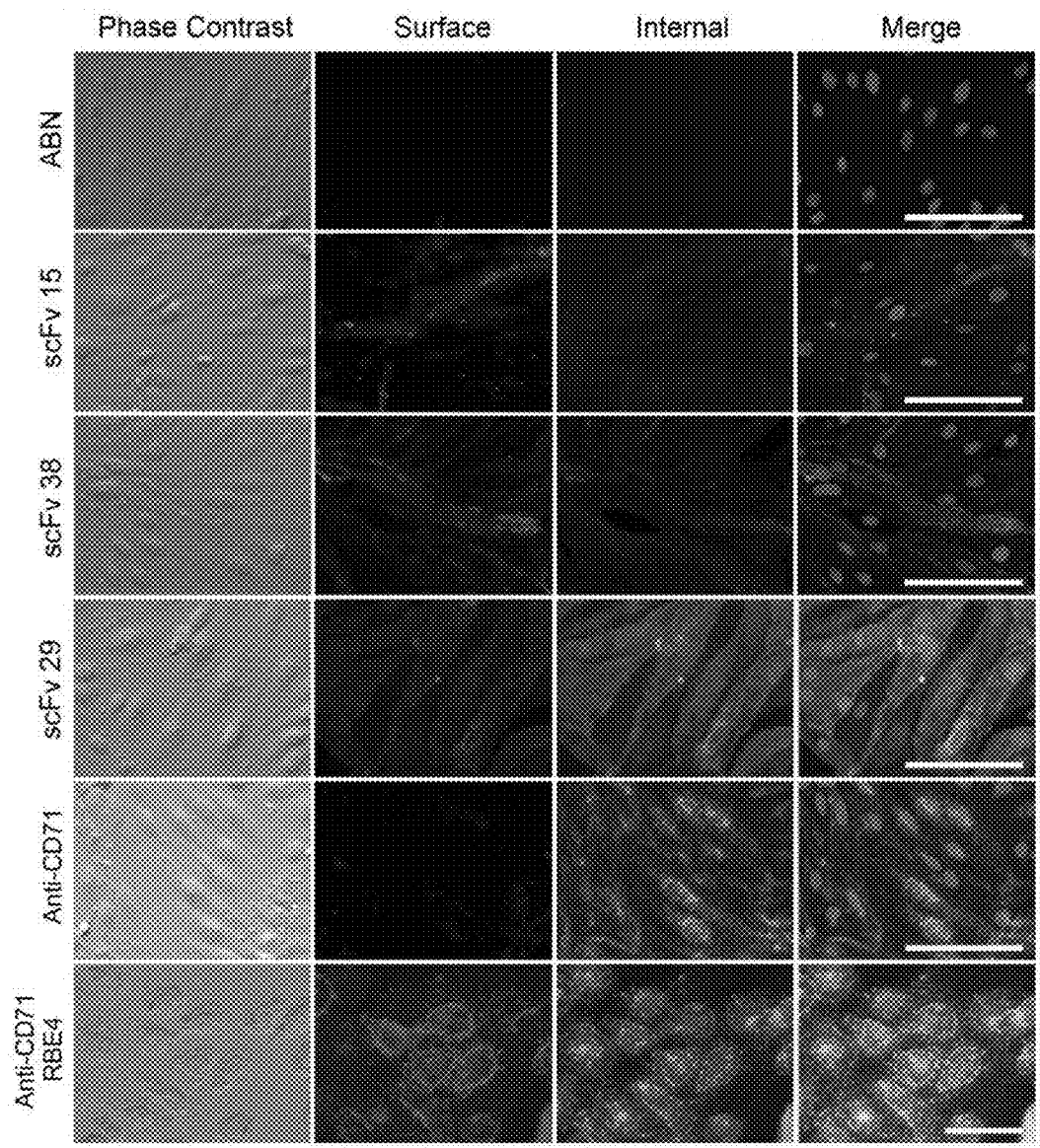
FIG. 3 is a set of images of an assay for antibody internalization. BMECs or RBE4 (last row only) cells were incubated with 100 μg/mL (~3 μM) of scFv pre-dimerized with 9E10 (anti-c-myc) first on ice for 30 minutes and then at 37° C. for 30 minutes. As an internalization positive control, an anti-CD71 (anti-transferrin receptor IgG) antibody was employed. The BMEC or RBE4 cell surface was subsequently labeled with Alexafluor594 (red) for 30 minutes. The cells were fixed with 4% paraformaldehyde, permeabilized with triton X100 and the interior of the cell labeled with Alexa Fluor® 488 (green). Subsequently the cells were labeled with the nuclear stain, DAPI (merged column only). Note the accumulated, punctate intracellular green fluorescence in the anti-CD71 samples indicative of internalized antibody, and the enhanced surface and internalized fluorescence visible in the RBE4 rat brain endothelial cell line. The percentage of RBE4 cells exhibiting multiple internalized vesicles per cell is 92±5% compared to 46±2% for primary BMECs, p<0.001. Scale bar is 50 μm.

Since one of the objectives of the screen design was to bias towards internalizing antibodies, the endocytosis capability of the three antibodies was assessed. Briefly, purified scFv38, scFv29, and scFv15 were pre-dimerized with an anti-c-myc antibody since scFv multimerization has been shown to help promote internalization and the antibodies were selected using the multivalent Fd phage display system [Wang, X. X., Y. K. Cho, and E. V. Shusta, Mining a yeast library for brain endothelial cell-binding antibodies. Nat. Methods, 2007. 4(2): p. 143-145; Adams, G. P., M. S. Tai, J. E. McCartney, J. D. Marks, et al., Avidity-mediated enhancement of in vivo tumor targeting by single-chain Fv dimers. Clin. Can. Res., 2006. 12(5): p. 1599-1605]. The pre-dimerized scFvs were incubated with BMECs on ice for 30 minutes and then placed at 37° C. for 30 minutes to allow for internalization. The antibody distribution was then visualized by a dual fluorophore detection to assay for both external and internal antibody localization (FIG. 3). ScFv38, scFv29, and scFv15 did not appear to internalize appreciably, although with limited overall in vitro labeling of scFv15, internalization could not be completely ruled out. In contrast, a positive control antibody, OX-26, that recognizes the rat transferrin receptor, which is known to internalize [Poul, M. A., B. Becerril, et al., 2000, supra], did demonstrate internalization in this assay as evidenced by punctate vesicles in the perinuclear and cytoplasmic regions of the cell.

In Vivo Organ Binding Distribution of scFv38, scFv29, and scFv15

Figure 4:
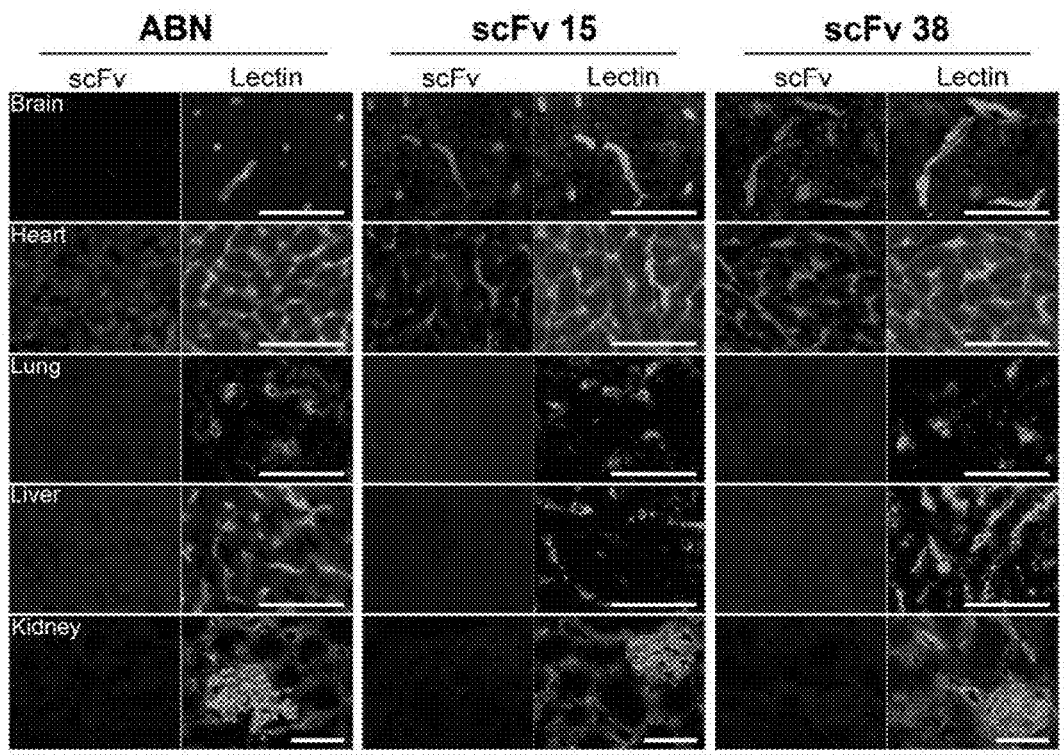
FIG. 4 discloses the tissue distribution of antibody binding. Purified ABN scFv (negative control), scFv15, and scFv38 were incubated on rat brain, heart, liver, lung or kidney tissue sections at a concentration of 100 μg/mL (~3 μM) except for kidney labeling which was done at 50 μg/mL (~1.5 μM) to limit nonspecific background. Both of these concentrations yielded clearly discernable labeling of the brain vasculature. The sections were co-labeled with FITC-conjugated IB4 lectin as an endothelial cell marker, except for kidney in which an anti-rat CD31 antibody was used to label kidney sections serial to the sections labeled with scFv. The scale bar is 50 μm.

Since the screen was performed in vitro and some interesting cellular binding selectivity was exhibited for clones scFv29, and scFv15, the in vivo organ binding distribution was assessed using rat tissue cryosections. First, purified scFv38, scFv29, and scFv15 were used to immunolabel rat brain sections (FIG. 4). Interestingly, scFv clones scFv38 and scFv15 clearly bind to brain capillaries having excellent co-localization with the vascular marker, IB4 lectin, but no brain capillary labeling was detected for scFv29 although this scFv produced the highest and most selective binding signal on cultured BMECs.

To assess the organ specificity of the scFv that bind to brain endothelial cells in vivo, scFv15 and scFv38 were also used to immunolabel rat heart, lung, liver, and kidney cryosections (FIG. 4). As predicted by the binding patterns in cultured cells in vitro (FIGS. 2b and 2c), scFv15 and scFv38 immunolabeled the heart vasculature. However, in contrast to the in vitro-based immunocytochemistry results, neither scFv15 or scFv38 appeared to bind the in vivo lung vasculature, nor did they immunolabel the in vivo kidney or liver vasculatures. Thus, the antigens targeted by these two antibodies are at the very least differentially expressed in the brain compared with these peripheral vascular beds. Taken together, scFv38 and scFv15 both target a BBB resident antigen in vivo and do so with vascular selectivity with respect to all peripheral organs tested other than heart.

Discussion

This study demonstrates that scFvs having the capability to selectively bind the BBB in vivo can be identified using the hydrocortisone-induced primary BMEC model as a phage display-based screening substrate. While other in vitro BBB models based on primary BMECs or immortalized BMECs have been used as screening substrates [Muruganandam, A., et al., 2001, supra] it was expected that the hydrocortisone-induced model might provide a more robust screening platform given the advantages in BBB phenotype previously demonstrated [Calabria, A. R., C. Weidenfeller, et al., 2006 supra; Perriere, N., S. Yousif, S. Cazaubon, N. Chaverot, et al., A functional in vitro model of rat blood-brain barrier for molecular analysis of efflux transporters. Brain Res., 2007. 1150: p. 1-13; Perriere, N., P. H. Demeuse, E. Garcia, A. Regina, et al., Puromycin-based purification of rat brain capillary endothelial cell cultures, Effect on the expression of blood-brain barrier-specific properties. J. Neurochem., 2005. 93(2): p. 279-289]. After evaluating roughly 400 phage clones by applying phage ELISA, phage immunocytochemistry and DNA sequence filters, the overall diversity was reduced to three scFvs capable of binding BMECs as soluble proteins. The imposition of these various evaluation filters, along with pre-subtraction and internalization screening pressures, likely contributed to the low numbers of recovered scFvs. Moreover, as a result of antibody affinity, antigen abundance and clonal expression bias, it is relatively commonplace for such screens to result in a limited diversity of targeting antibodies [Muruganandam, A., et al., 2001, supra; Poul, M. A., B. Becerril, et al., 2000, supra; Li, J. W., L. Feng, L. Fan, Y. Zha, et al., Targeting the brain with PEG-PLGA nanoparticles modified with phage-displayed peptides. Biomaterials, 2011. 32(21): p. 4943-4950]. While the resultant scFv diversity was lower than desired, it may be possible to further expand the diversity by performing pure binding screens rather than including internalization selection pressure. For example, employing a binding screen on the immortalized RBE4 brain endothelial cell line using a yeast display library yielded 34 different binding antibodies [Wang, X. X., Y. K. Cho, and E. V. Shusta, 2007, supra].

The screen was designed in an attempt to bias towards identification of endocytosing antibodies [Muruganandam, A., et al., 2001, supra; Poul, M. A., B. Becerril, et al., 2000, supra; Heitner, T., A. Moor, J. L. Garrison, C. Marks, et al., Selection of cell binding and internalizing epidermal growth factor receptor antibodies from a phage display library. J. Immunol. Methods, 2001. 248(1-2): p. 17-30; Florea, B. I., T. J. M. Molenaar, I. Bot, I. N. Michon, et al., Identification of an internalising peptide in differentiated Calu-3 cells by phage display technology; application to gene delivery to the airways. J. Drug Target., 2003. 11(7): p. 383-390], although the recovered scFvs did not appear to be capable of internalization, at least using the in vitro assay employed in FIG. 3. For the most part, internalization screens have been performed using immortalized cell lines or cancer cell lines [Poul, M. A., B. Becerril, et al., 2000, supra; Heitner, T., A. Moor, et al., 2001, supra] that endocytose avidly given their enhanced proliferative status. By comparison, primary rat BMECs were used as the screening platform in this study and these cells are fairly non-proliferative, as is the in vivo BBB [Calabria, A. R., C. Weidenfeller, et al., 2006 supra]. Moreover, one of the prevailing phenotypes of the in vivo BBB is a substantially reduced amount of vesicle-based trafficking [Stewart, P. A., Endothelial vesicles in the blood-brain barrier: Are they related to permeability? Cell. Mol. Neurobiol., 2000. 20(2): p. 149-163], a property that in our experience also appears to manifest itself in primary in vitro BBB models. This phenomenon can be visualized in FIG. 3, where both primary endothelial cells and the RBE4 immortalized endothelial cell line were assayed for anti-transferrin receptor antibody internalization. It can be seen that the amount of transferrin receptor labeling on the cell surface (red) and the number of cells possessing multiple internalized vesicles (green) is decreased in primary BMECs when compared to the highly proliferative immortalized RBE4 cell line (FIG. 3). Thus, the beneficial signal-to-noise often afforded by an internalization selection pressure was likely muted in the BMEC screen, leading to the identification of antibodies that either do not internalize, or do so sparingly in primary cultured BMECs. Interestingly, in an attempt to further explore the internalization capacity of scFv15 and scFv38 in the RBE4 cell line because of its enhanced endocytosis phenotype, it was found that scFv15 and scFv38 did not cross-react with the RBE4 cells. Therefore, while the primary culture based BMEC model used in the screen was apparently non-ideal for internalization screening, the model offered benefits in that scFv15 and scFv38 which interact with the BBB in vivo would not have been identified using the RBE4 cell line.

Pre-subtraction has been used to predispose screens toward cell-type specificity [Muruganandam, A., et al., 2001, supra; Heitner, T., A. Moor, et al., 2001, supra; Huie, M. A., M. C. Cheung, M. O. Muench, B. Becerril, et al., Antibodies to human fetal erythroid cells from a nonimmune phage antibody library. Proc. Natl. Acad. Sci. USA, 2001. 98(5): p. 2682-2687], and this approach was effective in this study as well. ScFv29 originated from the pre-subtraction screen and appeared to display BMEC specificity on the in vitro cultured cell screening substrates. ScFv15 also originated from the pre-subtraction screen and while it still bound to HECs and LECs, scFv15 still exhibited elevated binding to BMECs. When moving toward the in vivo environment in terms of binding the vasculature in rat brain tissue sections, scFv29 proved to bind an antigen that is expressed at detectable levels only in the cultured cells. This in vitro artifact is a well-known challenge of performing screens using in vitro cell-based platforms because, while a primary BMEC expression profile is more in vivo-like than an immortalized cell line, it is still substantially different from the true in vivo situation [Calabria, A. R. and E. V. Shusta, 2008, supra; Lyck, R., N. Ruderisch, A. G. Moll, O. Steiner, et al., Culture-induced changes in blood-brain barrier transcriptome: implications for amino-acid transporters in vivo. J. Cereb. Blood Flow Metab., 2009. 29(9): p. 1491-1502]. In particular, although the addition of hydrocortisone to the rat BMEC model does beneficially move many transcripts towards the in vivo BBB expression profile, some transcripts are also artificially upregulated as well [Calabria, A. R. and E. V. Shusta, 2008, supra]. This phenomenon, along with typical aberrant cellular regulation associated with in vitro culture can help explain the identification of scFvs like scFv29 that only bind in vitro. In contrast to scFv29, scFv15 and scFv38 bound brain capillaries in vivo. In addition, these two antibodies demonstrated binding to an antigen expressed in brain and heart vasculature that was not detected by scFv immunolabeling of the lung, liver, or kidney. Despite the heart cross-reactivity, there are very few if any potential brain targeting antibodies or peptides that have been demonstrated to have the BBB selectivity that is demonstrated by scFv15 and scFv38, as oftentimes the targeted receptors are ubiquitously expressed like the transferrin or insulin receptors [Stutz, C., X. Zhang, and E. Shusta, 2013, supra; Jones, A. R. and E. V. Shusta, 2007, supra]. While it remains to be determined whether or not scFv15 or scFv38 will transport into the brain parenchyma, it should be noted that simply targeting the BBB and providing a local drug reservoir, or internalizing into the BBB and using the endothelial cells as reservoirs for trophic molecules can also be beneficial for therapeutic efficacy [Chen, Y. H., M. Chang, and B. L. Davidson, Molecular signatures of disease brain endothelia provide new sites for CNS-directed enzyme therapy. Nat. Med., 2009. 15(10): p. 1215-U145; Bickel, U., T. Yoshikawa, and W. M. Pardridge, Delivery of peptides and proteins through the blood-brain barrier. Adv. Drug Deliv. Rev., 2001. 46(1-3): p. 247-279]. Thus, given their tissue selectivity, scFv15 and scFv38 offer promise as BBB targeting reagents, pending further in vivo evaluation of their targeting and transport attributes.

TABLE 1

Assessment of screen progress.

| | Pre-subtracted | | Non-subtracted | |
| --- | --- | --- | --- | --- |
| | Titer (cfu)$^a$ | Digestion Patterns$^b$ | Titer (cfu)$^a$ | Digestion Patterns$^b$ |
| Round 1 | $9.45 \times 10^3$ | | $8.98 \times 10^4$ | |
| Round 2 | $3.01 \times 10^5$ | 33/92 | $1.29 \times 10^6$ | 28/71 |
| Round 3 | $1.51 \times 10^6$ | 2/94 | $3.44 \times 10^5$ | 25/94 |

$^a$Phage titers from the internalized fraction of screens
$^b$The fraction of unique BstN1 digestion patterns

The invention claimed is:

1. A BBB-selective antibody comprising a peptide encoded by a DNA sequence comprising SEQ ID NO:7, SEQ ID NO:8, SEQ ID NO:9, SEQ ID NO:10, SEQ ID NO:11 and SEQ ID NO:12 or a DNA sequence comprising SEQ ID NO:19, SEQ ID NO:20, SEQ ID NO:21, SEQ ID NO:22, SEQ ID NO:23 and SEQ ID NO:24, wherein the antibody is connected to a pharmaceutical, therapeutic, or diagnostic compound.

2. A BBB-selective antibody comprising a protein encoded by SEQ ID NO:1 or 3.

3. The antibody of claim 1, wherein the antibody is engrafted within a full IgG scaffold of human or other species origin or a scFv scaffold of human or other species of origin.

4. The antibody of claim 1, wherein the antibody is connected to a pharmaceutical or therapeutic compound.

5. The antibody of claim 1, wherein the compound is a diagnostic compound.

6. A vector comprising a BBB-selective antibody of claim 1.

7. A microorganism comprising the vector of claim 6.

8. A method of targeting a pharmaceutical or therapeutic compound to the blood brain barrier of a subject comprising the steps of
   (a) obtaining a BBB-selective antibody attached to a pharmaceutical or therapeutic compound of claim 4 and
   (b) exposing the antibody of step (a) to a subject's brain.

9. The method of claim 8 wherein the pharmaceutical or therapeutic compound crosses the BBB after targeting.

10. The method of claim 8 wherein the therapeutic or pharmaceutical compound is delivered to the surface of the BBB after targeting.

11. A BBB-selective antibody comprising a peptide comprising SEQ ID NO:13, SEQ ID NO:14, SEQ ID NO:15, SEQ ID NO:16, SEQ ID NO:17 and SEQ ID NO:18 or comprising SEQ ID NO:25, SEQ ID NO:26, SEQ ID NO:27, SEQ ID NO:28, SEQ ID NO:29 and SEQ ID NO:30, wherein the antibody is connected to a pharmaceutical, therapeutic, or diagnostic compound.

12. A BBB-selective antibody comprising a peptide of SEQ ID NO:2 or SEQ ID NO:4, wherein the antibody is connected to a pharmaceutical, therapeutic, or diagnostic compound.

* * * * *

SEQUENCE LISTING

<160> NUMBER OF SEQ ID NOS: 30

<210> SEQ ID NO 1
<211> LENGTH: 708
<212> TYPE: DNA
<213> ORGANISM: Artificial Sequence
<220> FEATURE:
<223> OTHER INFORMATION: scFv 15

<400> SEQUENCE: 1
caggtgcagc tggtggagtc tgggggaggc ttggtccagc ctggggggtc cctgagactc    60
tcctgtgcag cctctggatt caccttagt aactattgga tgacctgggg ccgccaggct   120
ccagggaagg ggctggagtg ggtggccatc ataagccaag atggaagtga gaaatactat   180
gtggactctg tgcagggccg attcaccatc tccagagaca acgcgaagaa ctcactgtat   240

```
ctgcaaatga acagcctgac agccgaagac acggctgtgt attactgtgc gagagatcga    300
tatgattact ggggccaggg caccctggtc accgtctcct caggtggagg cggttcaggc    360
ggaggtggct ctggcggtgg cggatcgaat tttatgctga ctcaggaccc tgctgtgtct    420
gtggccttgg gacagacagt caggatcaca tgccaaggag acagcctcag aagctattat    480
gcaagctggt accagcagaa gccaggccag tcccctgtgc tggtcatcta tcaagataac    540
aagcggccct cagggatccc tgagcgattc tctggctcca gtctgggaa tacagccact     600 ctgaccatca gcgggaccca ggctatggat gaggctgagt atttctgtca ggcgtgggac    660
agcagcgctg tcgcgttcgg cggagggacc aaggtcaccg tcctaggt                 708
```

<210> SEQ ID NO 2
<211> LENGTH: 236
<212> TYPE: PRT
<213> ORGANISM: Artificial Sequence
<220> FEATURE:
<223> OTHER INFORMATION: scFv 15 Amino Acid Sequence
<400> SEQUENCE: 2

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Thr Trp Gly Arg Gln Ala Pro Gly Lys Gly Leu Glu Trp Val
        35                  40                  45

Ala Ile Ile Ser Gln Asp Gly Ser Glu Lys Tyr Tyr Val Asp Ser Val
    50                  55                  60

Gln Gly Arg Phe Thr Ile Ser Arg Asp Asn Ala Lys Asn Ser Leu Tyr
65                  70                  75                  80

Leu Gln Met Asn Ser Leu Thr Ala Glu Asp Thr Ala Val Tyr Tyr Cys
                85                  90                  95

Ala Arg Asp Arg Tyr Asp Tyr Trp Gly Gln Gly Thr Leu Val Thr Val
            100                 105                 110

Ser Ser Gly Gly Gly Gly Ser Gly Gly Gly Ser Gly Gly Gly Gly
        115                 120                 125

Ser Asn Phe Met Leu Thr Gln Asp Pro Ala Val Ser Val Ala Leu Gly
    130                 135                 140

Gln Thr Val Arg Ile Thr Cys Gln Gly Asp Ser Leu Arg Ser Tyr Tyr
145                 150                 155                 160

Ala Ser Trp Tyr Gln Gln Lys Pro Gly Gln Ser Pro Val Leu Val Ile
                165                 170                 175

Tyr Gln Asp Asn Lys Arg Pro Ser Gly Ile Pro Glu Arg Phe Ser Gly
            180                 185                 190

Ser Lys Ser Gly Asn Thr Ala Thr Leu Thr Ile Ser Gly Thr Gln Ala
        195                 200                 205

Met Asp Glu Ala Glu Tyr Phe Cys Gln Ala Trp Asp Ser Ser Ala Val
    210                 215                 220

Ala Phe Gly Gly Gly Thr Lys Val Thr Val Leu Gly
225                 230                 235
```

<210> SEQ ID NO 3
<211> LENGTH: 729
<212> TYPE: DNA
<213> ORGANISM: Artificial Sequence
<220> FEATURE:
<223> OTHER INFORMATION: scFv 38

<400> SEQUENCE: 3

```
caggtgcagc tggtggagtc tgggggaggc gtggtccagg ccggggcatc cctgagagtc    60
tcctgtgcag catctggatt cagtttgact agctatggga tgcactgggt ccgccaggct   120
ccaggcaagg gactggagtg gtggcttttt atttcgtctg atggtagtga taagtactat   180
gtagactctg tgaagggccg attcaccatc tccagagaca cttccaagaa catgatgtat   240
ctgcaaatga acagcctgac aactgaggat acggctgtgt attactgtgc gaaagactgg   300
ggcagcaact ggtacctctt tgactactgg ggccagggaa ccctggtcac cgtctcctca   360
ggtggaggcg gttcaggcgg aggtggctct ggcggtggcg gatcggacat ccagatgacc   420
cagtctcctt ccaccctgtc tgcagctgta ggagacacaa tcaccattac ttgtcgggcg   480
agtcaagatt tcaggaactg gttagcctgg tatcagctga accaggaaa agccccccaag   540
ccctgatct atggtgcatc cactttgcaa catggggtcc catccaggtt cagcggcagt   600
gggtctggga cagatttctc tctcactatc agtagcctgc agcctgagga ttttgcaact   660
tactttttgtc aacaggctca cagtttccct cccactttcg gcggagggac caagctggag   720
atcaaacgt                                                          729
```

<210> SEQ ID NO 4
<211> LENGTH: 243
<212> TYPE: PRT
<213> ORGANISM: Artificial Sequence
<220> FEATURE:
<223> OTHER INFORMATION: scFv 38 Amino Acid Sequence

<400> SEQUENCE: 4

```
Gln Val Gln Leu Val Glu Ser Gly Gly Gly Val Val Gln Ala Gly Ala
1               5                   10                  15

Ser Leu Arg Val Ser Cys Ala Ala Ser Gly Phe Ser Leu Thr Ser Tyr
            20                  25                  30

Gly Met His Trp Val Arg Gln Ala Pro Gly Lys Gly Leu Glu Trp Val
        35                  40                  45

Ala Phe Ile Ser Ser Asp Gly Ser Asp Lys Tyr Tyr Val Asp Ser Val
    50                  55                  60

Lys Gly Arg Phe Thr Ile Ser Arg Asp Thr Ser Lys Asn Met Met Tyr
65                  70                  75                  80

Leu Gln Met Asn Ser Leu Thr Thr Glu Asp Thr Ala Val Tyr Tyr Cys
                85                  90                  95

Ala Lys Asp Trp Gly Ser Asn Trp Tyr Leu Phe Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Thr Leu Ser Ala Ala Val Gly Asp Thr Ile Thr Ile Thr Cys Arg Ala
145                 150                 155                 160

Ser Gln Asp Phe Arg Asn Trp Leu Ala Trp Tyr Gln Leu Lys Pro Gly
                165                 170                 175

Lys Ala Pro Lys Pro Leu Ile Tyr Gly Ala Ser Thr Leu Gln His Gly
            180                 185                 190

Val Pro Ser Arg Phe Ser Gly Ser Gly Ser Gly Thr Asp Phe Ser Leu
        195                 200                 205

Thr Ile Ser Ser Leu Gln Pro Glu Asp Phe Ala Thr Tyr Phe Cys Gln
```

```
                210                 215                 220
Gln Ala His Ser Phe Pro Pro Thr Phe Gly Gly Gly Thr Lys Leu Glu
225                 230                 235                 240

Ile Lys Arg

<210> SEQ ID NO 5
<211> LENGTH: 22
<212> TYPE: DNA
<213> ORGANISM: Artificial Sequence
<220> FEATURE:
<223> OTHER INFORMATION: The forward primer sequence

<400> SEQUENCE: 5
tttttggaga ttttcaacgt ga                                          22

<210> SEQ ID NO 6
<211> LENGTH: 27
<212> TYPE: DNA
<213> ORGANISM: Artificial Sequence
<220> FEATURE:
<223> OTHER INFORMATION: The reverse primer sequence.

<400> SEQUENCE: 6
gaattttctg tatgaggttt tgctaaa                                     27

<210> SEQ ID NO 7
<211> LENGTH: 30
<212> TYPE: DNA
<213> ORGANISM: Artificial Sequence
<220> FEATURE:
<223> OTHER INFORMATION: CDR H1 of scFv 15

<400> SEQUENCE: 7 ggattcaccct ttagtaacta ttggatgacc                                 30

<210> SEQ ID NO 8
<211> LENGTH: 51
<212> TYPE: DNA
<213> ORGANISM: Artificial Sequence
<220> FEATURE:
<223> OTHER INFORMATION: CDR H2 of scFv 15

<400> SEQUENCE: 8
atcataagcc aagatggaag tgagaaatac tatgtggact ctgtgcaggg c          51

<210> SEQ ID NO 9
<211> LENGTH: 15
<212> TYPE: DNA
<213> ORGANISM: Artificial Sequence
<220> FEATURE:
<223> OTHER INFORMATION: CDR H3 of scFv 15

<400> SEQUENCE: 9
gatcgatatg attac                                                  15

<210> SEQ ID NO 10
<211> LENGTH: 33
<212> TYPE: DNA
<213> ORGANISM: Artificial Sequence
<220> FEATURE:
<223> OTHER INFORMATION: CDR L1 of scFv 15

<400> SEQUENCE: 10
caaggagaca gcctcagaag ctattatgca agc                              33
```

<210> SEQ ID NO 11
<211> LENGTH: 21
<212> TYPE: DNA
<213> ORGANISM: Artificial Sequence
<220> FEATURE:
<223> OTHER INFORMATION: CDR L2 of scFv 15

<400> SEQUENCE: 11
caagataaca agcggccctc a                    21

<210> SEQ ID NO 12
<211> LENGTH: 27
<212> TYPE: DNA
<213> ORGANISM: Artificial Sequence
<220> FEATURE:
<223> OTHER INFORMATION: CDR L3 of scFv 15

<400> SEQUENCE: 12
caggcgtggg acagcagcgc tgtcgcg              27

<210> SEQ ID NO 13
<211> LENGTH: 10
<212> TYPE: PRT
<213> ORGANISM: Artificial Sequence
<220> FEATURE:
<223> OTHER INFORMATION: CDR H1 of scFv 15

<400> SEQUENCE: 13

Gly Phe Thr Phe Ser Asn Tyr Trp Met Thr
1               5                   10

<210> SEQ ID NO 14
<211> LENGTH: 17
<212> TYPE: PRT
<213> ORGANISM: Artificial Sequence
<220> FEATURE:
<223> OTHER INFORMATION: CDR H2 of scFv 15

<400> SEQUENCE: 14

Ile Ile Ser Gln Asp Gly Ser Glu Lys Tyr Tyr Val Asp Ser Val Gln
1               5                   10                  15
Gly

<210> SEQ ID NO 15
<211> LENGTH: 5
<212> TYPE: PRT
<213> ORGANISM: Artificial Sequence
<220> FEATURE:
<223> OTHER INFORMATION: CDR H3 of scFv 15

<400> SEQUENCE: 15

Asp Arg Tyr Asp Tyr
1               5

<210> SEQ ID NO 16
<211> LENGTH: 11
<212> TYPE: PRT
<213> ORGANISM: Artificial Sequence
<220> FEATURE:
<223> OTHER INFORMATION: CDR L1 of scFv 15

<400> SEQUENCE: 16

Gln Gly Asp Ser Leu Arg Ser Tyr Tyr Ala Ser
1               5                   10

```
<210> SEQ ID NO 17
<211> LENGTH: 7
<212> TYPE: PRT
<213> ORGANISM: Artificial Sequence
<220> FEATURE:
<223> OTHER INFORMATION: CDR L2 of scFv15

<400> SEQUENCE: 17

Gln Asp Asn Lys Arg Pro Ser
1               5

<210> SEQ ID NO 18
<211> LENGTH: 9
<212> TYPE: PRT
<213> ORGANISM: Artificial Sequence
<220> FEATURE:
<223> OTHER INFORMATION: CDR L3 of scFv 15

<400> SEQUENCE: 18

Gln Ala Trp Asp Ser Ser Ala Val Ala
1               5

<210> SEQ ID NO 19
<211> LENGTH: 30
<212> TYPE: DNA
<213> ORGANISM: Artificial Sequence
<220> FEATURE:
<223> OTHER INFORMATION: CDR H1 of scFv 38

<400> SEQUENCE: 19
ggattcagtt tgactagcta tgggatgcac                                       30

<210> SEQ ID NO 20
<211> LENGTH: 51
<212> TYPE: DNA
<213> ORGANISM: Artificial Sequence
<220> FEATURE:
<223> OTHER INFORMATION: CDR H2 of scFv 38

<400> SEQUENCE: 20
tttatttcgt ctgatggtag tgataagtac tatgtagact ctgtgaaggg c               51

<210> SEQ ID NO 21
<211> LENGTH: 33
<212> TYPE: DNA
<213> ORGANISM: Artificial Sequence
<220> FEATURE:
<223> OTHER INFORMATION: CDR H3 of scFv 38

<400> SEQUENCE: 21
gactggggca gcaactggta cctctttgac tac                                   33

<210> SEQ ID NO 22
<211> LENGTH: 33
<212> TYPE: DNA
<213> ORGANISM: Artificial Sequence
<220> FEATURE:
<223> OTHER INFORMATION: CDR L1 of scFv 38

<400> SEQUENCE: 22
cgggcgagtc aagatttcag gaactggtta gcc                                   33

<210> SEQ ID NO 23
<211> LENGTH: 21
<212> TYPE: DNA
<213> ORGANISM: Artificial Sequence
<220> FEATURE:
```

```
<223> OTHER INFORMATION: CDR L2 of scFv 38

<400> SEQUENCE: 23
ggtgcatcca ctttgcaaca t                                              21

<210> SEQ ID NO 24
<211> LENGTH: 27
<212> TYPE: DNA
<213> ORGANISM: Artificial Sequence
<220> FEATURE:
<223> OTHER INFORMATION: CDR L3 of scFv 38

<400> SEQUENCE: 24
caacaggctc acagtttccc tcccact                                        27

<210> SEQ ID NO 25
<211> LENGTH: 10
<212> TYPE: PRT
<213> ORGANISM: Artificial Sequence
<220> FEATURE:
<223> OTHER INFORMATION: CDR H1 of scFv 38

<400> SEQUENCE: 25

Gly Phe Ser Leu Thr Ser Tyr Gly Met His
1               5                   10

<210> SEQ ID NO 26
<211> LENGTH: 17
<212> TYPE: PRT
<213> ORGANISM: Artificial Sequence
<220> FEATURE:
<223> OTHER INFORMATION: CDR H2 of scFv 38

<400> SEQUENCE: 26

Phe Ile Ser Ser Asp Gly Ser Asp Lys Tyr Tyr Val Asp Ser Val Lys
1               5                   10                  15
Gly

<210> SEQ ID NO 27
<211> LENGTH: 11
<212> TYPE: PRT
<213> ORGANISM: Artificial Sequence
<220> FEATURE:
<223> OTHER INFORMATION: CDR H3 of scFv 38

<400> SEQUENCE: 27

Asp Trp Gly Ser Asn Trp Tyr Leu Phe Asp Tyr
1               5                   10

<210> SEQ ID NO 28
<211> LENGTH: 11
<212> TYPE: PRT
<213> ORGANISM: Artificial Sequence
<220> FEATURE:
<223> OTHER INFORMATION: CDR L1 of scFv 38

<400> SEQUENCE: 28

Arg Ala Ser Gln Asp Phe Arg Asn Trp Leu Ala
1               5                   10

<210> SEQ ID NO 29
<211> LENGTH: 7
<212> TYPE: PRT
<213> ORGANISM: Artificial Sequence
<220> FEATURE:
<223> OTHER INFORMATION: CDR L2 of scFv 38
```

```
<400> SEQUENCE: 29

Gly Ala Ser Thr Leu Gln His
1               5

<210> SEQ ID NO 30
<211> LENGTH: 9
<212> TYPE: PRT
<213> ORGANISM: Artificial Sequence
<220> FEATURE:
<223> OTHER INFORMATION: CDR L3 of scFv 38

<400> SEQUENCE: 30

Gln Gln Ala His Ser Phe Pro Pro Thr
1               5
```